(12) United States Patent
Tamano et al.

(10) Patent No.: US 11,883,407 B2
(45) Date of Patent: Jan. 30, 2024

(54) MEDICAMENT FOR THE TREATMENT OF CHRONIC COUGH

(71) Applicant: Shionogi & Co., Ltd., Osaka (JP)

(72) Inventors: Ryuta Tamano, Osaka (JP); Erika Kasai, Osaka (JP); Sayaka Miyazaki, Osaka (JP); Katsue Magari, Osaka (JP)

(73) Assignee: SHIONOGI & CO., LTD., Osaka (JP)

( * ) Notice: Subject to any disclaimer, the term of this patent is extended or adjusted under 35 U.S.C. 154(b) by 5 days.

(21) Appl. No.: 17/281,741

(22) PCT Filed: Oct. 4, 2019

(86) PCT No.: PCT/JP2019/039275
§ 371 (c)(1),
(2) Date: Mar. 31, 2021

(87) PCT Pub. No.: WO2020/071530
PCT Pub. Date: Apr. 9, 2020

(65) Prior Publication Data
US 2021/0393640 A1    Dec. 23, 2021

(30) Foreign Application Priority Data

Oct. 5, 2018 (JP) ................ 2018-189791
Mar. 12, 2019 (JP) ................ 2019-044943
Sep. 25, 2019 (JP) ................ 2019-173841

(51) Int. Cl.
*A61K 31/53* (2006.01)
*A61P 11/14* (2006.01)

(52) U.S. Cl.
CPC ............ *A61K 31/53* (2013.01); *A61P 11/14* (2018.01)

(58) Field of Classification Search
CPC ................. A61K 31/53; A61P 11/14
See application file for complete search history.

(56) References Cited

U.S. PATENT DOCUMENTS

| | | | |
|---|---|---|---|
| 10,111,883 B1 * | 10/2018 | Garceau | A61P 27/00 |
| 2016/0115151 A1 | 4/2016 | Kai | |
| 2017/0362199 A1 * | 12/2017 | Kai | A61P 43/00 |
| 2018/0280388 A1 * | 10/2018 | Ford | A61K 47/44 |

FOREIGN PATENT DOCUMENTS

| | | |
|---|---|---|
| CN | 1915311 | 2/2007 |
| CN | 105582039 | 5/2016 |
| EP | 3 009 432 | 4/2016 |
| WO | 2006/012639 | 2/2006 |
| WO | 2014/117274 | 8/2014 |
| WO | 2015/027212 | 2/2015 |
| WO | 2016/091776 | 6/2016 |
| WO | 2017/058645 | 4/2017 |
| WO | 2019/064079 | 4/2019 |
| WO | 2019/219674 | 11/2019 |

OTHER PUBLICATIONS

Abdulqawi et al. (The Lancet (2015) 385:1198-1205). (Year: 2015).*
The Japanese Respiratory Society, Committee for the Guidelines for Management of Cough, 2nd Edition, Guidelines for Management of Cough, 2nd Edition, 2012.
Niimi, N., "Cough Hypersensitivity Syndrome", The Journal of the Japanese Society of Internal Medicine 2016; vol. 105, No. 9, pp. 1565-1577.
Shioya, T., "Pathogenesis of Cough", The Japanese Journal of Chest Diseases 2015, vol. 74, No. 11, pp. 1179-1188.
Nakano, C. et al., "Diagnosis of chronic cough", Respiratory Medicine 2016; vol. 29. No. 2, pp. 104-107.
Pacheco et al., "Refractory Chronic Cough: New Perspectives in Diagnosis and Treatment", Arch Bronconeumol. 2013, vol. 49. No. 4, pp. 151-157.
Hulme et al., "Psychological profile of individuals presenting with chronic cough", ERJ Open Res. 2017; vol. 3, 00099-2016.
McGarvey, L.P.A., "Does Idiopathic Cough Exist?", Lung 2008, Vo. 186, Suppl. 1, S78-S81.
Levine, B.M., "Systematic evaluation and treatment of chronic cough in a community setting", Allergy Asthma Proc. 2008, vol. 29, No. 3, pp. 336-342.
Wirkner et al., "P2X$_3$ Receptor Involvement in Pain States", Mol. Neurobiol. 2007, vol. 36, pp. 165-183.
Fowles et al., "Tussive challenge with ATP and AMP: does it reveal cough hypersensitivity?", Eur. Respir. J., 2017, vol. 49, 1601452.
Basoglu et al., "Effects of Aerosolized Adenosine 5'-Triphosphate vs Adenosine 5'-Monophosphate on Dyspnea and Airway Caliber in Healthy Nonsmokers and Patients With Asthma", Chest 2005; vol. 128, No. 4, pp. 1905-1909.
Smith et al., "The Effect of P2X3 Antagonism (AF-219) on Experimentally Evoked Cough in Healthly Volunteers and Chronic Cough Patients", Thorax, British Thoracic Society Winter Meeting 2016, Abstract S27; vol. 71, Issue Suppl. 3.

(Continued)

*Primary Examiner* — Marcos L Sznaidman
(74) *Attorney, Agent, or Firm* — Wenderoth, Lind & Ponack, L.L.P.

(57) ABSTRACT

Provided is a pharmaceutical composition for treating chronic cough, which has substantially no side effects of taste disturbance.
A pharmaceutical composition for treating chronic cough, comprising a compound represented by Formula (I):

[Chemical Formula 1]

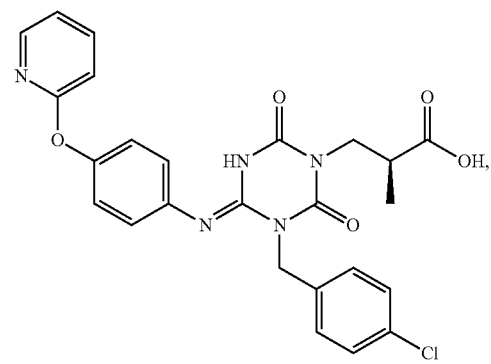

or a pharmaceutically acceptable salt thereof.

11 Claims, 1 Drawing Sheet

(56) References Cited

OTHER PUBLICATIONS

Jarvis et al., "ATP-gated P2X cation-channels", Neuropharmacology 2009, vol. 56, pp. 208-215.
Adriaensen et al., "Sensory input to the central nervous system from the lungs and airways: A prominent role for purinergic signalling via P2X2/4 receptors", Auton. Neurosci. 2015, vol. 191, pp. 39-47.
Wan et al., "P2X$_{2/3}$ receptor activity of rat nodose ganglion neurons contributing to myocardial ischemic nociceptive signaling", Auton. Neurosci. 2010, vol. 158, pp. 58-64.
Sato et al., "Distribution of TRPVs, P2X3, and Parvalbumin in the Human Nodose Ganglion", Cell Mol. Neurobiol. 2014, vol. 34, pp. 851-858.
Brouns et al., "Neurochemical characterisation of sensory receptors in airway smooth muscle: comparison with pulmonary neuroepithelial bodies", Histochem. Cell Biol. 2006, vol. 125, pp. 351-367.
Undem et al., "Subtypes of vagal afferent C-fibres in guinea-pig lungs", J. Physiol. 2004; 556(Pt 3), pp. 905-917.
Weigand et al., "A role for ATP in bronchoconstriction-induced activation of guinea pig vagal intrapulmonary C-fibres", J Physiol., 2012, vol. 590, No. 16, pp. 4109-4120.
Muller et al., "The purinergic receptor subtype P2Y$_2$ mediates chemotaxis of neutrophils and fibroblasts in fibrotic lung disease", Oncotarget 2017, vol. 8, No. 22, pp. 35962-35972.
Kobayashi et al., "Elevated uric acid and adenosine triphosphate concentrations in bronchoalveolar lavage fluid of eosinophilic pneumonia", Allergol. Int. 2017, vol. 66, Suppl:S27-S34.
Abdulqawi et al., "P2X3 receptor antagonist (AF-219) in refractory chronic cough: a randomised, double-blind, placebo-controlled phase 2 study", Lancet 2015, vol. 385, pp. 1198-1205.
Finger et al., "ATP Signaling Is Crucial for Communication from Taste Buds to Gustatory Nerves". Science 2005, vol. 310, pp. 1495-1499.
Garceau et al., "BLU-5937: A selective P2X3 antagonist with potent anti-tussive effect and no taste alteration", Pulmonary Pharmacology & Therapeutics 56, 2019, pp. 56-62.
Smith et al., "Mk-7264, A P2x3 Receptor Antagonist, Reduces Cough Frequency In Patients With Refractory Chronic Cough: Results From A Randomized, Controlled, Phase 2b Clinical Trial", Am. J. Respir. Crit. Care Med., 2017, vol. 195, A7608.
Smith et al., "Gefapixant, a P2X3 receptor antagonist, for the treatment of refractory or unexplained chronic cough: a randomised, double-blind, controlled, parallel-group, phase 2b trial", Lancet Respir. Med., 2020, Published Online Feb. 25, 2020. https://doi.org/10.1016/S2213-2600(19)30471-0.
Morice et al., "The Effect of Gefapixant, a P2X3 antagonist, on Cough Reflex Sensitivity: A randomised placebo-controlled study", European Respiratory Journal, 2019, in press (https://doi.org/10.1183/13993003.00493-2019).
Richards et al., "Action of MK-7264 (gefapixant) at human P2X3 and P2X2/3 receptors and in vivo efficacy in models of sensitisation", Br. J. Pharmacol. 2019, vol. 176, pp. 2279-2291.
Morice et al., "A7648. Safety and Efficacy of BAY 1817080, a P2X3 Receptor Antagonist, in Patients with Refractory Chronic Cough (RCC)", ATS International Conf., Pennsylvania Convention Center, May 20, 2020, Abstract A7648.
Ford, A.P., "In pursuit of P2X3 antagonist: novel therapeutics for chronic pain and afferent sensitization", Purinergic Signalling 2012, vol. 8, Suppl. 1, pp. S3-S26.
Abdulqawi et al., "Inhibition of ATP-gated P2X3 channels by AF-219: An effective anti-tussive mechanism in chronic cough", European Respiratory Society Annual Congress 2013, Abstract 7026, Publ. No. 1965.
Ford, A.P., "P2X3 antagonism by AF-219 for sensitization-driven symptoms: POC results in distressing respiratory. somatosensory & visceral conditions", Afferent Pharmaceuticals, Pain Summit 2014.
Ford et al., "The therapeutic promise of ATP antagonism an P2X3 receptors in respiratory and urological disorders", Frontiers in Cellular Neuroscience, vol. 7, Article 267, 2013, pp. 1-10.
Kinnamon et al., "A taste for ATP: neurotransmission in taste buds", Frontiers in Cellular Neuroscience, vol. 7, Article 264, 2013, pp. 1-7.
Ryan et al., "Gabapentin for refractory chronic cough: a randomised, double-blind, placebo-controlled trial", Lancet 2012, vol. 380, pp. 1583-1589.
Morice et al., "Safety and Efficacy of BAY 1817080, a P2X3 Receptor Antagonist, in Patients with Refractory Chronic Cough (RCC)", Am J Respir. Crit. Care Med. 2020; vol. 201, A7648.
A 12-Week Study in Participants with Refractory Chronic Cough (MK-7264-012), Afferent Pharma., Inc., ClinicalTrials.gov NCT02612610.
BLU-5937 Phase 1 Data and Corporate Update, Bellus Health, Nov. 20, 2018.
"P2X3 Antagonist Demonstrates Efficacy Against Refractory Chronic Cough in Phase II (POC)", Evotec SE News Release, Jul. 25, 2019.
McGarvey et al., "Two Phase 3 Randomized Clinical Trials of Gefapixant, a P2X3 Receptor Antagonist, in Refractory or Unexplained Chronic Cough (COUGH-1 and COUGH-2)", ERS International Congress 2020 virtual.
Turner et al., "Chronic cough: ATP, afferent pathways and hypersensitivity", Eur. Respir J., 2019; vol. 54, pp. 1-5.
Garceau et al., "BLU-5937 a Highly Selective P2X3 Homotrimeric Receptor Antagonist with Improved Taste Safety Profile in Healthy Subjects", ATS International Conference, Dallas, Texas, May 21, 2019, Abstract A7396 / p. 556.
Martinez et al., "A2638—The Treatment of Chronic Cough in Idiopathic Pulmonary Fibrosis Patients with Gefapixant, a P2x3 Receptor Antagonist", ATS International Conference, Dallas, Texas, May 20, 2019, Abstract A2638.
PURINES 2014—International Conference on Signalling, Drugs and Targets, Bonn, Germany, Jul. 23-27, 2014, pp. 1-320.
Abdulqawi et al., "Inhibition of ATP-gates P2X3 channels by AF-219: An effective anti-tussive mechanism in chronic cough", 2013 ERS, Abstract 1965.
Chung, K.F., "Approach to chronic cough: the neuropathic basis for cough hypersensitivity syndrome", J. Thorac. Dis., 2014, vol. 6, No. S7, pp. S699-S707.
Niimi et al., "Phase 2a randomized, double-blind, placebo-controlled, crossover study of P2X3 receptor antagonist S-0600918: effects on health-related quality of life in patients with refractory chronic cough", ATS 2020, virtual, Aug. 5, 2020, Abstract A7647.
Sher et al., "Sustained Antitussive Effect of AF-219 in Chronic Cough Patients Treated for 8 Weeks", ACAAI-2016, Eur. Res. J., 2016, vol. 48 OA1976, pp. 1-18, Abstract O035.
Gibson et al., "Management of Chronic refractory cough", BMJ 2015;351:h5590, pp. 1-12.
Wang et al., "Druggable negative allosteric site of P2X3 receptors", PNAS, May 8, 2018, vol. 115, No. 19, pp. 4939-4944.
Niimi et al., "Phase 2a randomised, double-blind, placebo-controlled, crossover study of a novel P2X3 receptor antagonist S-600918 in patients with refractory chronic cough", ERS 2019, Abstract 20945.
Keller et al., "Translating Cough Mechanisms Into Better Cough Suppressants", CHEST, 2017, vol. 152, No. 4, pp. 833-841.
Hussain et al., "Dose Selection for Two Phase 3 Randomized Controlled Trials (COUGH-1 and COUGH-2) in Refractory of Unexplained Chronic Cough", ATS2020, Virtual, Aug. 5-10, 2020.
Morice et al., "Safety and Efficacy of BAY 1817080, a P$_2$X$_3$ Receptor Antagonist, in Patients with Refractory Chronic Cough", ATS2020 International Conference Virtual Platform.
Highlights of the 11th International Cough Symposium, Lancet Respir. Med. 2021 Published Online Mar. 9, 2021, https://doi.org/10.1016/S2213-2600(21)00130-2.
Pavord et al., "Management of chronic cough", Lancet 2008; vol. 371, pp. 1375-1384.
Muccino et al., "Design and rationale of two phase 3 randomised controlled trials (COUGH-1 and COUGH-2) of gefapixant, a P2X3 receptor antagonist, in refractory or unexplained chronic cough", ERJ Open Res., 2020; vol. 6, 00284-2020, pp. 1-11.
Smith et al., "Chronic Cough", NEJM, vol. 375, No. 16, pp. 1544-1551.

(56) References Cited

OTHER PUBLICATIONS

Abstracts: ISAN 2015—A meeting of the International Society for Autonomic Neuroscience held in conjunction with the American Autonomic Society, the European Federation of Autonomic Societies and the Japanese Society for Neurovegetative Research, Autonomic Neuroscience: Basic and Clinical, 2015, vol. 192, pp. 1-55.
Chung et al., "Prevalence, pathogenesis, and causes of chronic cough", Lancet 2008, vol. 371, pp. 1364-1374.
The JRS Guidelines for the Management of Cough and Sputum, The Japanese Respiratory Society, 2019.
"I Love Clean Air", 19th Japan Cough Study Group Program / Abstracts, Oct. 28, 2017.
Research and Development at Shionogi, Shionogi & Co., Ltd., Mar. 14, 2019, pp. 1-154.
Search Report issued in Russian Patent Application No. 2021112143.
Extended European Search Report dated Jun. 7, 2022 in corresponding European Patent Application No. 19869380.6.

\* cited by examiner

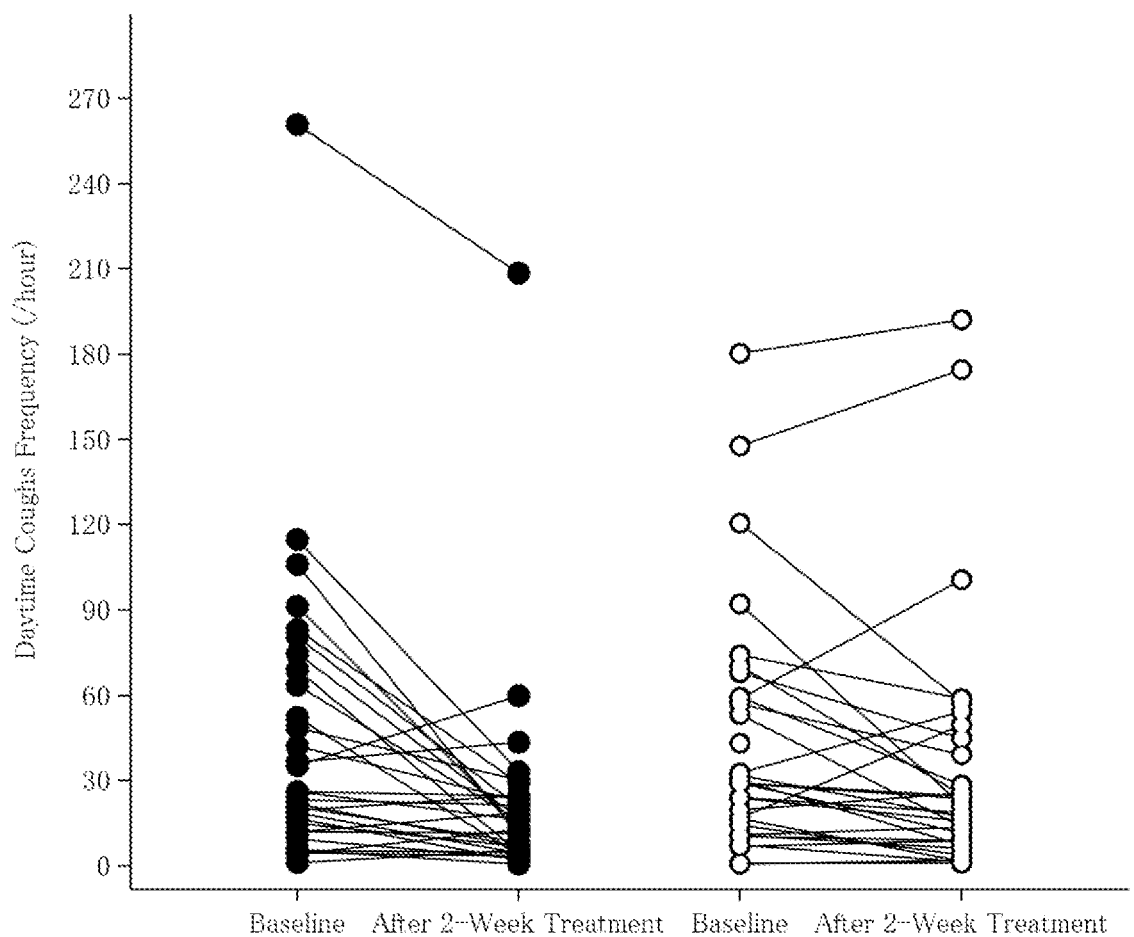

MEDICAMENT FOR THE TREATMENT OF CHRONIC COUGH

TECHNICAL FIELD

The present invention relates to the treatment of diseases involving P2X receptors, particularly P2X$_3$ and/or P2X$_{2/3}$ receptors. In particular, the present invention relates to a pharmaceutical composition comprising P2X$_3$ and/or P2X$_{2/3}$ receptor antagonists for treating chronic cough, acute cough or sub-acute cough.

BACKGROUND ART

Cough is one of the biological defense reflexes for expelling sputum and foreign substances in the respiratory tract. However, it leads to a decrease in quality of life (QOL) when persisting excessively. In the guidelines on cough made by the Japanese Respiratory Society, chronic cough is defined as a cough lasting for 8 weeks or longer (Non-patent Document 1). As the underlying causes of chronic cough, cough variant asthma, atopic cough, gastroesophageal reflux disease, and sinobronchial syndrome are prevalent in Japan. However, cases of multiple underlying causes, or unexplained (idiopathic) cases are also included (Non-patent Documents 1-4). The prevalence of chronic cough in Japan is about 2% to 10%, although it varies depending on the report (Non-patent Documents 3, 5-8).

There are no approved drugs for chronic cough. While the treatment of cough is based on identifying the underlying disease as much as possible and performing a treatment specific to the cause (Non-patent Document 1), codeine, dextromethorphan, and the like, which are non-specific antitussive therapeutic drugs, are used to improve the exhaustion of the patient and the QOL (Non-patent Document 1). However, central antitussives also suppress cough that is necessary as a biological defense mechanism, and side effects such as constipation and drowsiness often occur (Non-patent Document 2). Therefore, an effective and safe drug that can be administered long-term is desired (Non-patent Document 1).

ATP functions not only as an intracellular energy substrate but also as a messenger outside the cell, and is known to evoke pain when locally administered to humans and animals (Non-patent Document 9), and to induce a cough reflex through inhalation in humans (Non-patent Documents 10-12). Among purinergic receptors, the ion channel-coupled subtypes that use ATP as a ligand are called P2X receptors, and seven subtypes, P2X$_1$ to P2X$_7$, are known (Non-patent Document 13). Of these, the P2X$_3$ receptor is mainly expressed in small primary afferent nerves with C fibers and Aδ fibers associated with sensory reception and transmission, and has been suggested to have a strong involvement in cough reflex and pain.

The mechanism of promoting cough reflex by P2X$_3$ receptor activation is considered to be as follows. When sensory nerve endings (Aδ or C fibers) distributed on the surface of the airway wall are mechanically or chemically stimulated, mediators such as ATP are released, which activate/sensitize P2X$_3$ receptors. The signal generated by the activation of P2X$_3$ receptors is thought to be transmitted mainly to the cough center of the medulla oblongata via nerve firing of the ganglion inferius (nodose ganglion), a vagal nerve branch, which then evokes a cough reaction.

The expression of the P2X$_3$ receptor has been reported in bronchial C fibers and inferior ganglion cells of humans, rats and mice (Non-patent Document 14-17). In addition, in an electrophysiological study using lung tissue of guinea pigs, an action potential in the nerve fibers of the ganglion inferius that are mainly projected from the lower respiratory tract such as the lungs and bronchi, has been reported to occur with the treatment of lung tissue with ATP or αβ-methylene ATP, which is an P2X$_3$ receptor-selective agonist (Non-patent Document 18). Furthermore, this action potential has been reported to be almost completely suppressed by the P2X receptor antagonist TNP-ATP and the tool compound AF-353, which is a P2X$_3$ receptor-selective inhibitor (Non-patent Document 19), which suggests that the ATP-P2X$_3$ receptor signal is involved in the cough reflex mechanism.

The cough reflex is known to be induced by inhalation of ATP in humans as well (Non-patent Documents 10-12). It has also been reported that higher ATP levels than in healthy adults are observed in the bronchoalveolar lavage fluid of patients with idiopathic pulmonary fibrosis and patients with acute eosinophilic pneumonia, which are known as diseases associated with cough symptoms (Non-patent Documents 20 and 21). This suggests that ATP is an important mediator for inducing cough in humans as well. Furthermore, the number of ATP inhalation-induced cough reflexes in patients with chronic cough, asthma and chronic obstructive pulmonary disease is higher than in healthy adults (Non-patent Documents 10-12), which suggests that sensitivity to ATP is increased in diseases associated with cough symptoms.

In addition, Patent Document 1 suggests that the P2X$_3$/P2X$_{2/3}$ receptor-selective antagonist (5-({3-phenoxybenzyl)[(1S)-1,2,3,4-tetrahydro-1-naphthalenyl]amino}carbonyl)-1,2,4-benzenetricarboxylic acid (A-317491) inhibits activity of the pulmonary vagal afferent C and A fibers by α,βmATP, and is effective in the treatment of lung diseases (for example, asthma and chronic obstructive pulmonary disease). However, the effectiveness of cough treatment in humans is not described.

On the other hand, Non-patent Document 22 reports the results of a phase II clinical trial of AF-219 (Gefapixant), which is a P2X$_3$ and P2X$_{2/3}$ antagonist, and describes that the frequency of daytime cough was reduced by 75% in patients with chronic cough compared to the placebo group. In addition, it reported that dysgeusia (88%, 21 out of 24 cases) and hypogeusia (54%, 13 out of 24 cases) were confirmed as adverse events in patients administered with AF-219, and that all patients developed some kind of taste-related disorder. Moreover, it also reported that 6 of the participants discontinued the trial due to a taste disturbance (hypogeusia or dysgeusia).

In addition, a large number of clinical trial protocols for AF-219 (MK-7264, Gefapixant) and their results are recorded on ClinicalTrials.gov. For example, the results of a trial in which 253 of the 367 candidate patients were randomly assigned to a twice daily oral administration group of a placebo, 7.5 mg, 20 mg or 50 mg of AF-219 to confirm the therapeutic effect after 12 weeks, have been published under the identification number NCT02612610. Among the trial results, it was published that as one of the adverse events, for example, dysgeusia was confirmed in each dose group: 9.52% (7.5 mg administration group, 6 out of 63 cases), 33.33% (20 mg administration group, 21 out of 63 cases) and 47.62% (50 mg administration group, 30 out of 63 cases). In addition, some of these trial results are also described in Patent Documents 2 and 3 and Non-patent Document 25.

In Non-patent Document 23, the results of a taste sensory evaluation on P2X$_2$ knockout mice, P2X$_3$ knockout mice, and P2X$_2$/P2X$_3$ double knockout mice have been published.

Imidazopyridine compounds (Patent Document 4), thiazole-substituted benzamide compounds (Patent Document 5), and the like are known as $P2X_3$ and/or $P2X_{2/3}$ receptor antagonists. In addition, it has been published on ClinicalTrials.gov that clinical trials on the treatment of chronic cough using the $P2X_3$ receptor antagonist BLU-5937 are being conducted.

On Nov. 20, 2018, the results of the Phase I clinical trial of BLU-5937 were released on Bellus' website. Taste-related adverse events during single administration and repeated administration were disclosed: at 100 mg (n=16), taste changes were confirmed in 1 subject (6.3%), at 400 mg (n=16), taste changes were confirmed in 6 subjects (37.5%) and partial taste loss in 1 subject (6.25%), at 800 mg (n=8), taste changes were confirmed in 5 subjects (62.5%) and partial taste loss in 1 subject (12.5%), and at 1200 mg (n=8), taste changes were confirmed in 2 subjects (25%). It has also been published that all taste-related adverse events were transient and sporadic, with one case being moderate and the remaining cases being mild. In addition, Non-patent Document 24 discloses activity and selectivity of BLU-5937 on human, rat and guinea pig $P2X_3$ and $R2X_{2/3}$ receptors. However, its chemical structural formula has not been published.

Furthermore, it is published on ClinicalTrials.gov that clinical trials on the treatment of chronic cough using the $P2X_3$ receptor antagonists BAY-1817080 and BAY-1902607 are being conducted. On Jul. 25, 2019, it was released on Evotec's website that a reduction in the number of coughs per 24 hours was confirmed in the results of the Phase 1/2a clinical trial of BAY-1817080. However, the rate of decrease in cough was not revealed, nor was the rate of taste-related adverse events published. Furthermore, the chemical structural formula of BAY-1817080 has not been published. In addition, the clinical results and chemical structural formula of BAY-1902607 have not been published.

Moreover, Patent Document 6 discloses a large number of compounds exhibiting $P2X_3$ and/or $P2X_{2/3}$ receptor antagonist activity and describes them as being effective in treating, alleviating the symptoms of, or preventing, for example, pain such as neuropathic pain, chronic obstructive pulmonary disease, asthma, bronchospasm, chronic cough, and the like. However, there is no specific description regarding the therapeutic effect on chronic obstructive pulmonary disease, asthma, bronchospasm, chronic cough and the like.

As described above, while a treatment of chronic cough with $P2X_3$ and/or $P2X_{2/3}$ receptor antagonists is under development, no drug has yet been found that it is effective in humans and has no taste-related side effects (e.g., dysgeusia, hypogeusia, ageusia). Therefore, the development of a safe drug having a therapeutic effect on chronic cough and having no taste-related side effects or reduced taste-related side effects, is desired.

PRIOR ART REFERENCES

Patent Document

[Patent Document 1] International Publication No. WO 2006/012639
[Patent Document 2] International Publication No. WO 2015/027212
[Patent Document 3] International Publication No. WO 2017/058645
[Patent Document 4] International Publication No. WO 2014/117274
[Patent Document 5] International Publication No. WO 2016/091776
[Patent Document 6] International Publication No. WO 2014/200078

Non-Patent Document

[Non-patent Document 1] The Japanese Respiratory Society, Committee for the Guidelines for Management of Cough, 2nd Edition, Guidelines for Management of Cough, 2nd Edition, 2012
[Non-patent Document 2] The Journal of the Japanese Society of Internal Medicine 2016; 105(9): 1565-77
[Non-patent Document 3] The Japanese Journal of Chest Diseases 2015; 74(11): 1179-88
[Non-patent Document 4] Respiratory Medicine 2016; 29(2): 104-7
[Non-patent Document 5] Arch Bronconeumol 2013; 49(4): 151-7
[Non-patent Document 6] ERJ Open Res 2017; 3: 00099-2016.
[Non-patent Document 7] Lung. 2008; 186 Suppl 1: S78-81
[Non-patent Document 8] Allergy Asthma Proc 2008; 29(3): 336-42
[Non-patent Document 9] Mol Neurobiol 2007; 36: 165-83
[Non-patent Document 10] Eur Respir J 2017; 49: 1601452
[Non-patent Document 11] Chest 2005; 128(4): 1905-9
[Non-patent Document 12] Thorax, British Thoracic Society Winter Meeting 2016: S27; Volume 71, Issue Suppl 3
[Non-patent Document 13] Neuropharmacology 2009; 56: 208-15
[Non-patent Document 14] Auton Neurosci 2015; 191: 39-47
[Non-patent Document 15] Auton Neurosci 2010; 158: 58-64
[Non-patent Document 16] Cell Mol Neurobiol 2014; 34: 851-8
[Non-patent Document 17] Histochem Cell Biol 2006; 125: 351-67
[Non-patent Document 18] J Physiol 2004; 556 (Pt 3): 905-17
[Non-patent Document 19] J Physiol 2012; 590(16): 4109-20
[Non-patent Document 20] Oncotarget 2017; 8(22): 35962-72
[Non-patent Document 21] Allergol Int 2017; 66 (Suppl): S27-34
[Non-patent Document 22] Lancet 2015; 385: 1198-205
[Non-patent Document 23] Science 2005; 310: 1495-1499
[Non-patent Document 24] Pulmonary Pharmacology & Therapeutics 56 (2019) 56-62
[Non-patent Document 25] Am J Respir Crit Care Med 2017; 195: A7608

SUMMARY OF THE INVENTION

Problems to be Solved by the Invention

An object of the present invention is to provide a pharmaceutical composition for the treatment of chronic cough, which has excellent $P2X_3$ receptor antagonist activity, has no taste-related side effects, or has reduced taste-related side effects.

Means for Solving the Problem

As a result of repeated studies to solve the above problem, the present inventors have found that among the $P2X_3$ and/or P2X$_{2/3}$ receptor antagonists described in Patent Document 6, a specific compound (Compound I-127) has excellent P2X$_3$ receptor antagonist activity, is expected to be clinically effective in humans, and has substantially no taste-related side effects, which led to the completion of the present invention.

The present invention relates to the following (1) to (4), (4-a) to (4-t), (4-n'), (4A) to (4E), (5) to (8), (8-a) to (8-t), (8-n'), (8A) to (8E), (9) to (12), (12-a) to (12-t), (12-n'), (12A) to (12E), (13) to (16), (16-a) to (16-t), (16-n'), (16A) to (16E), (17) to (23), (23-a) to (23-t), (23-n'), (24), (24B) to (24E) and (25) to (29).

(1)
A pharmaceutical composition for treating chronic cough, comprising a compound represented by

[Chemical Formula 1]

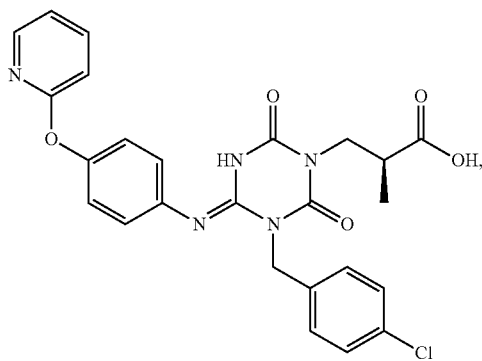

(I)

or a pharmaceutically acceptable salt thereof.

(2)
The pharmaceutical composition according to (1), wherein the chronic cough is a refractory chronic cough.

(3)
The pharmaceutical composition according to (1) or (2), which has substantially no side effects of taste disturbance by the administration of the pharmaceutical composition.

(4)
The pharmaceutical composition according to any one of (1) to (3), wherein the daily dose of the active ingredient of the pharmaceutical composition is 10 mg to 450 mg.

(4-a)
The pharmaceutical composition according to any one of (1) to (3), wherein the daily dose of the active ingredient of the pharmaceutical composition is 10 mg to 300 mg.

(4-b)
The pharmaceutical composition according to any one of (1) to (3), wherein the daily dose of the active ingredient of the pharmaceutical composition is 20 mg to 300 mg.

(4-c)
The pharmaceutical composition according to any one of (1) to (3), wherein the daily dose of the active ingredient of the pharmaceutical composition is 30 mg to 300 mg.

(4-d)
The pharmaceutical composition according to any one of (1) to (3), wherein the daily dose of the active ingredient of the pharmaceutical composition is 50 mg to 300 mg.

(4-e)
The pharmaceutical composition according to any one of (1) to (3), wherein the daily dose of the active ingredient of the pharmaceutical composition is 70 mg to 300 mg.

(4-f)
The pharmaceutical composition according to any one of (1) to (3), wherein the daily dose of the active ingredient of the pharmaceutical composition is 100 mg to 300 mg.

(4-g)
The pharmaceutical composition according to any one of (1) to (3), wherein the daily dose of the active ingredient of the pharmaceutical composition is 150 mg to 300 mg.

(4-h)
The pharmaceutical composition according to any one of (1) to (3), wherein the daily dose of the active ingredient of the pharmaceutical composition is 10 mg to 150 mg.

(4-i)
The pharmaceutical composition according to any one of (1) to (3), wherein the daily dose of the active ingredient of the pharmaceutical composition is 20 mg to 150 mg.

(4-j)
The pharmaceutical composition according to any one of (1) to (3), wherein the daily dose of the active ingredient of the pharmaceutical composition is 30 mg to 150 mg.

(4-k)
The pharmaceutical composition according to any one of (1) to (3), wherein the daily dose of the active ingredient of the pharmaceutical composition is 50 mg to 150 mg.

(4-l)
The pharmaceutical composition according to any one of (1) to (3), wherein the daily dose of the active ingredient of the pharmaceutical composition is 70 mg to 150 mg.

(4-m)
The pharmaceutical composition according to any one of (1) to (3), wherein the daily dose of the active ingredient of the pharmaceutical composition is 100 mg to 150 mg.

(4-n)
The pharmaceutical composition according to any one of (1) to (3), wherein the daily dose of the active ingredient of the pharmaceutical composition is 150 mg.

(4-n')
The pharmaceutical composition according to any one of (1) to (3), wherein the daily dose of the active ingredient of the pharmaceutical composition is 300 mg.

(4-o)
The pharmaceutical composition according to any one of (1) to (3), wherein the daily dose of the active ingredient of the pharmaceutical composition is 100 mg.

(4-p)
The pharmaceutical composition according to any one of (1) to (3), wherein the daily dose of the active ingredient of the pharmaceutical composition is 70 mg.

(4-q)
The pharmaceutical composition according to any one of (1) to (3), wherein the daily dose of the active ingredient of the pharmaceutical composition is 50 mg.

(4-r)
The pharmaceutical composition according to any one of (1) to (3), wherein the daily dose of the active ingredient of the pharmaceutical composition is 30 mg.

(4-s)
The pharmaceutical composition according to any one of (1) to (3), wherein the daily dose of the active ingredient of the pharmaceutical composition is 20 mg.

(4-t)
The pharmaceutical composition according to any one of (1) to (3), wherein the daily dose of the active ingredient of the pharmaceutical composition is 10 mg.

(4A)
The pharmaceutical composition according to any one of (1) to (4), (4-a) to (4-t) and (4-n'), which is administered once daily.

(4B)
The pharmaceutical composition according to any one of (1) to (4), (4-a) to (4-t) and (4-n'), which is administered once daily after a meal.

(4C)
The pharmaceutical composition according to any one of (1) to (4), (4-a) to (4-t) and (4-n'), which is administered once daily at bedtime.

(4D)
The pharmaceutical composition according to any one of (1) to (4), (4-a) to (4-t) and (4-n'), which is administered once daily before a meal.

(4E)
The pharmaceutical composition according to any one of (1) to (4), (4-a) to (4-t) and (4-n'), which is administered once daily between meals.

(5)
A method for treating chronic cough, the method comprising a step of administering an effective amount of a compound represented by Formula (I):

[Chemical Formula 2]

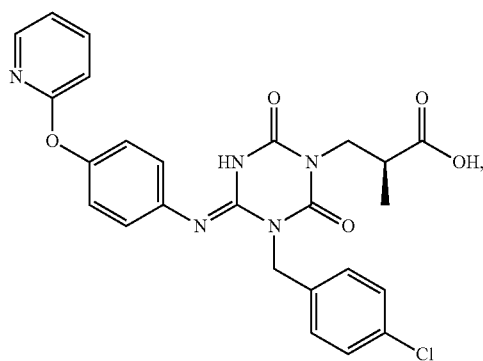

(I)

or a pharmaceutically acceptable salt thereof to an individual in need of treatment of chronic cough.

(6)
The method of treatment according to (5), wherein the chronic cough is a refractory chronic cough.

(7)
The method of treatment according to (5) or (6), which has substantially no side effects of taste disturbance by the administration of the compound represented by Formula (I) or a pharmaceutically acceptable salt thereof.

(8)
The method of treatment according to any one of (5) to (7), wherein the daily dose of the active ingredient is 10 mg to 450 mg.

(8-a)
The method of treatment according to any one of (5) to (7), wherein the daily dose of the active ingredient is 10 mg to 300 mg.

(8-b)
The method of treatment according to any one of (5) to (7), wherein the daily dose of the active ingredient is 20 mg to 300 mg.

(8-c)
The method of treatment according to any one of (5) to (7), wherein the daily dose of the active ingredient is 30 mg to 300 mg.

(8-d)
The method of treatment according to any one of (5) to (7), wherein the daily dose of the active ingredient is 50 mg to 300 mg.

(8-e)
The method of treatment according to any one of (5) to (7), wherein the daily dose of the active ingredient is 70 mg to 300 mg.

(8-f)
The method of treatment according to any one of (5) to (7), wherein the daily dose of the active ingredient is 100 mg to 300 mg.

(8-g)
The method of treatment according to any one of (5) to (7), wherein the daily dose of the active ingredient is 150 mg to 300 mg.

(8-h)
The method of treatment according to any one of (5) to (7), wherein the daily dose of the active ingredient is 10 mg to 150 mg.

(8-i)
The method of treatment according to any one of (5) to (7), wherein the daily dose of the active ingredient is 20 mg to 150 mg.

(8-j)
The method of treatment according to any one of (5) to (7), wherein the daily dose of the active ingredient is 30 mg to 150 mg.

(8-k)
The method of treatment according to any one of (5) to (7), wherein the daily dose of the active ingredient is 50 mg to 150 mg.

(8-l)
The method of treatment according to any one of (5) to (7), wherein the daily dose of the active ingredient is 70 mg to 150 mg.

(8-m)
The method of treatment according to any one of (5) to (7), wherein the daily dose of the active ingredient is 100 mg to 150 mg.

(8-n)
The method of treatment according to any one of (5) to (7), wherein the daily dose of the active ingredient is 150 mg.

(8-n')
The method of treatment according to any one of (5) to (7), wherein the daily dose of the active ingredient is 300 mg.

(8-o)
The method of treatment according to any one of (5) to (7), wherein the daily dose of the active ingredient is 100 mg.

(8-p)
The method of treatment according to any one of (5) to (7), wherein the daily dose of the active ingredient is 70 mg.

(8-q)
The method of treatment according to any one of (5) to (7), wherein the daily dose of the active ingredient is 50 mg.

(8-r)
The method of treatment according to any one of (5) to (7), wherein the daily dose of the active ingredient is 30 mg.

(8-s)
The method of treatment according to any one of (5) to (7), wherein the daily dose of the active ingredient is 20 mg.

(8-t)

The method of treatment according to any one of (5) to (7), wherein the daily dose of the active ingredient is 10 mg.

(8A)

The pharmaceutical composition according to any one of (5) to (8), (8-a) to (8-t) and (8-n'), which is administered once daily.

(8B)

The pharmaceutical composition according to any one of (5) to (8), (8-a) to (8-t) and (8-n'), which is administered once daily after a meal.

(8C)

The pharmaceutical composition according to any one of (5) to (8), (8-a) to (8-t) and (8-n'), which is administered once daily at bedtime.

(8D)

The pharmaceutical composition according to any one of (5) to (8), (8-a) to (8-t) and (8-n'), which is administered once daily before a meal.

(8E)

The pharmaceutical composition according to any one of (5) to (8), (8-a) to (8-t) and (8-n'), which is administered once daily between meals.

(9)

Use of a compound represented by Formula (I):

[Chemical Formula 3]

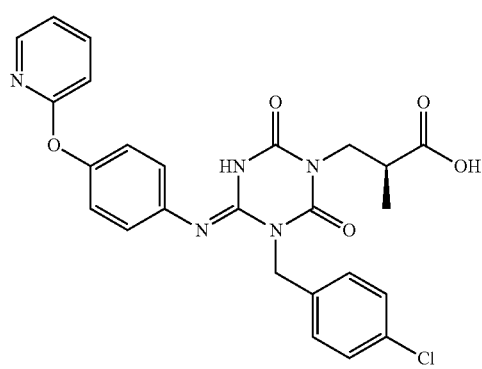

(I)

or a pharmaceutically acceptable salt thereof for the manufacture of a medicament for treating chronic cough.

(10)

The use according to (9), wherein the chronic cough is a refractory chronic cough.

(11)

The use according to (9) or (10), which has substantially no side effects of taste disturbance by the administration of the compound represented by Formula (I) or a pharmaceutically acceptable salt thereof.

(12)

The use according to any one of (9) to (11), wherein the daily dose of the active ingredient is 10 mg to 450 mg.

(12-a)

The use according to any one of (9) to (11), wherein the daily dose of the active ingredient is 10 mg to 300 mg.

(12-b)

The use according to any one of (9) to (11), wherein the daily dose of the active ingredient is 20 mg to 300 mg.

(12-c)

The use according to any one of (9) to (11), wherein the daily dose of the active ingredient is 30 mg to 300 mg.

(12-d)

The use according to any one of (9) to (11), wherein the daily dose of the active ingredient is 50 mg to 300 mg.

(12-e)

The use according to any one of (9) to (11), wherein the daily dose of the active ingredient is 70 mg to 300 mg.

(12-f)

The use according to any one of (9) to (11), wherein the daily dose of the active ingredient is 100 mg to 300 mg.

(12-g)

The use according to any one of (9) to (11), wherein the daily dose of the active ingredient is 150 mg to 300 mg.

(12-h)

The use according to any one of (9) to (11), wherein the daily dose of the active ingredient is 10 mg to 150 mg.

(12-i)

The use according to any one of (9) to (11), wherein the daily dose of the active ingredient is 20 mg to 150 mg.

(12-j)

The use according to any one of (9) to (11), wherein the daily dose of the active ingredient is 30 mg to 150 mg.

(12-k)

The use according to any one of (9) to (11), wherein the daily dose of the active ingredient is 50 mg to 150 mg.

(12-l)

The use according to any one of (9) to (11), wherein the daily dose of the active ingredient is 70 mg to 150 mg.

(12-m)

The use according to any one of (9) to (11), wherein the daily dose of the active ingredient is 100 mg to 150 mg.

(12-n)

The use according to any one of (9) to (11), wherein the daily dose of the active ingredient is 150 mg.

(12-n')

The use according to any one of (9) to (11), wherein the daily dose of the active ingredient is 300 mg.

(12-o)

The use according to any one of (9) to (11), wherein the daily dose of the active ingredient is 100 mg.

(12-p)

The use according to any one of (9) to (11), wherein the daily dose of the active ingredient is 70 mg.

(12-q)

The use according to any one of (9) to (11), wherein the daily dose of the active ingredient is 50 mg.

(12-r)

The use according to any one of (9) to (11), wherein the daily dose of the active ingredient is 30 mg.

(12-s)

The use according to any one of (9) to (11), wherein the daily dose of the active ingredient is 20 mg.

(12-t)

The use according to any one of (9) to (11), wherein the daily dose of the active ingredient is 10 mg.

(12A)

The pharmaceutical composition according to any one of (9) to (12), (12-a) to (12-t) and (12-n), which is administered once daily.

(12B)

The pharmaceutical composition according to any one of (9) to (12), (12-a) to (12-t) and (12-n), which is administered once daily after a meal.

(12C)

The pharmaceutical composition according to any one of (9) to (12), (12-a) to (12-t) and (12-n), which is administered once daily at bedtime.

(12D)

The pharmaceutical composition according to any one of (9) to (12), (12-a) to (12-t) and (12-n), which is administered once daily before a meal.

(12E)

The pharmaceutical composition according to any one of (9) to (12), (12-a) to (12-t) and (12-n), which is administered once daily between meals.

(13)

A compound represented by Formula (I):

[Chemical Formula 4]

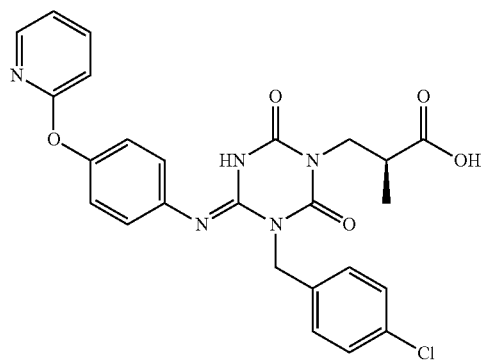

(I)

or a pharmaceutically acceptable salt thereof, for use in the treatment of chronic cough.

(14)

The compound according to (13) or a pharmaceutically acceptable salt thereof, wherein the chronic cough is a refractory chronic cough.

(15)

The compound according to (13) or (14) or a pharmaceutically acceptable salt thereof, which has substantially no side effects of taste disturbance by the administration of the compound represented by Formula (I) or a pharmaceutically acceptable salt thereof.

(16)

The compound according to any one of (13) to (15) or a pharmaceutically acceptable salt thereof, wherein the daily dose of the active ingredient is 10 mg to 450 mg.

(16-a)

The compound according to any one of (13) to (15) or a pharmaceutically acceptable salt thereof, wherein the daily dose of the active ingredient is 10 mg to 300 mg.

(16-b)

The compound according to any one of (13) to (15) or a pharmaceutically acceptable salt thereof, wherein the daily dose of the active ingredient is 20 mg to 300 mg.

(16-c)

The compound according to any one of (13) to (15) or a pharmaceutically acceptable salt thereof, wherein the daily dose of the active ingredient is 30 mg to 300 mg.

(16-d)

The compound according to any one of (13) to (15) or a pharmaceutically acceptable salt thereof, wherein the daily dose of the active ingredient is 50 mg to 300 mg.

(16-e)

The compound according to any one of (13) to (15) or a pharmaceutically acceptable salt thereof, wherein the daily dose of the active ingredient is 70 mg to 300 mg.

(16-f)

The compound according to any one of (13) to (15) or a pharmaceutically acceptable salt thereof, wherein the daily dose of the active ingredient is 100 mg to 300 mg.

(16-g)

The compound according to any one of (13) to (15) or a pharmaceutically acceptable salt thereof, wherein the daily dose of the active ingredient is 150 mg to 300 mg.

(16-h)

The compound according to any one of (13) to (15) or a pharmaceutically acceptable salt thereof, wherein the daily dose of the active ingredient is 10 mg to 150 mg.

(16-i)

The compound according to any one of (13) to (15) or a pharmaceutically acceptable salt thereof, wherein the daily dose of the active ingredient is 20 mg to 150 mg.

(16-j)

The compound according to any one of (13) to (15) or a pharmaceutically acceptable salt thereof, wherein the daily dose of the active ingredient is 30 mg to 150 mg.

(16-k)

The compound according to any one of (13) to (15) or a pharmaceutically acceptable salt thereof, wherein the daily dose of the active ingredient is 50 mg to 150 mg.

(16-l)

The compound according to any one of (13) to (15) or a pharmaceutically acceptable salt thereof, wherein the daily dose of the active ingredient is 70 mg to 150 mg.

(16-m)

The compound according to any one of (13) to (15) or a pharmaceutically acceptable salt thereof, wherein the daily dose of the active ingredient is 100 mg to 150 mg.

(16-n)

The compound according to any one of (13) to (15) or a pharmaceutically acceptable salt thereof, wherein the daily dose of the active ingredient is 150 mg.

(16-n')

The compound according to any one of (13) to (15) or a pharmaceutically acceptable salt thereof, wherein the daily dose of the active ingredient is 300 mg.

(16-o)

The compound according to any one of (13) to (15) or a pharmaceutically acceptable salt thereof, wherein the daily dose of the active ingredient is 100 mg.

(16-p)

The compound according to any one of (13) to (15) or a pharmaceutically acceptable salt thereof, wherein the daily dose of the active ingredient is 70 mg.

(16-q)

The compound according to any one of (13) to (15) or a pharmaceutically acceptable salt thereof, wherein the daily dose of the active ingredient is 50 mg.

(16-r)

The compound according to any one of (13) to (15) or a pharmaceutically acceptable salt thereof, wherein the daily dose of the active ingredient is 30 mg.

(16-s)

The compound according to any one of (13) to (15) or a pharmaceutically acceptable salt thereof, wherein the daily dose of the active ingredient is 20 mg.

(16-t)

The compound according to any one of (13) to (15) or a pharmaceutically acceptable salt thereof, wherein the daily dose of the active ingredient is 10 mg.

(16A)

The pharmaceutical composition according to any one of (13) to (16), (16-a) to (16-t) and (16-n'), which is administered once daily.

(16B)
The pharmaceutical composition according to any one of (13) to (16), (16-a) to (16-t) and (16-n'), which is administered once daily after a meal.
(16C)
The pharmaceutical composition according to any one of (13) to (16), (16-a) to (16-t) and (16-n'), which is administered once daily at bedtime.
(16D)
The pharmaceutical composition according to any one of (13) to (16), (16-a) to (16-t) and (16-n'), which is administered once daily before a meal.
(16E)
The pharmaceutical composition according to any one of (13) to (16), (16-a) to (16-t) and (16-n'), which is administered once daily between meals.
(17)
A pharmaceutical composition for treating chronic cough, comprising a compound or a pharmaceutically acceptable salt thereof having 200-fold or more selectivity for a human $P2X_3$ receptor inhibitory activity over a human $P2X_{2/3}$ receptor inhibitory activity, and having substantially no side effects of taste disturbance in humans.
(18)
A pharmaceutical composition comprising the compound represented by Formula (I) or a pharmaceutically acceptable salt thereof, wherein taste disturbance, a side effect related to the treatment, is reduced compared to other $P2X_3$ and/or $P2X_{2/3}$ receptor antagonists having a therapeutic effect on chronic cough.
(19)
The pharmaceutical composition according to (18), wherein the other $P2X_3$ and/or $P2X_{2/3}$ receptor antagonist having a therapeutic effect on chronic cough is Gefapixant.
(20)
The pharmaceutical composition according to (18), wherein the other $P2X_3$ and/or $P2X_{2/3}$ receptor antagonist having a therapeutic effect on chronic cough is BLU-5937.
(21)
The pharmaceutical composition according to (18), wherein the other $P2X_3$ and/or $P2X_{2/3}$ receptor antagonist having a therapeutic effect on chronic cough is BAY-1817080.
(22)
The pharmaceutical composition according to (18), wherein the other $P2X_3$ and/or $P2X_{2/3}$ receptor antagonist having a therapeutic effect on chronic cough is BAY-1902607.
(23)
The pharmaceutical composition according to any one of (16) to (22), wherein the daily dose of the active ingredient is 10 mg to 450 mg.
(23-a)
The pharmaceutical composition according to any one of (18) to (22), wherein the daily dose of the active ingredient of the pharmaceutical composition is 10 mg to 300 mg.
(23-b)
The pharmaceutical composition according to any one of (18) to (22), wherein the daily dose of the active ingredient of the pharmaceutical composition is 20 mg to 300 mg.
(23-c)
The pharmaceutical composition according to any one of (18) to (22), wherein the daily dose of the active ingredient of the pharmaceutical composition is 30 mg to 300 mg.
(23-d)
The pharmaceutical composition according to any one of (18) to (22), wherein the daily dose of the active ingredient of the pharmaceutical composition is 50 mg to 300 mg.
(23-e)
The pharmaceutical composition according to any one of (18) to (22), wherein the daily dose of the active ingredient of the pharmaceutical composition is 70 mg to 300 mg.
(23-f)
The pharmaceutical composition according to any one of (18) to (22), wherein the daily dose of the active ingredient of the pharmaceutical composition is 100 mg to 300 mg.
(23-g)
The pharmaceutical composition according to any one of (18) to (22), wherein the daily dose of the active ingredient of the pharmaceutical composition is 150 mg to 300 mg.
(23-h)
The pharmaceutical composition according to any one of (18) to (22), wherein the daily dose of the active ingredient of the pharmaceutical composition is 10 mg to 150 mg.
(23-i)
The pharmaceutical composition according to any one of (18) to (22), wherein the daily dose of the active ingredient of the pharmaceutical composition is 20 mg to 150 mg.
(23-j)
The pharmaceutical composition according to any one of (18) to (22), wherein the daily dose of the active ingredient of the pharmaceutical composition is 30 mg to 150 mg.
(23-k)
The pharmaceutical composition according to any one of (18) to (22), wherein the daily dose of the active ingredient of the pharmaceutical composition is 50 mg to 150 mg.
(23-l)
The pharmaceutical composition according to any one of (18) to (22), wherein the daily dose of the active ingredient of the pharmaceutical composition is 70 mg to 150 mg.
(23-m)
The pharmaceutical composition according to any one of (18) to (22), wherein the daily dose of the active ingredient of the pharmaceutical composition is 100 mg to 150 mg.
(23-n)
The pharmaceutical composition according to any one of (18) to (22), wherein the daily dose of the active ingredient of the pharmaceutical composition is 150 mg.
(23-n')
The pharmaceutical composition according to any one of (18) to (22), wherein the daily dose of the active ingredient of the pharmaceutical composition is 300 mg.
(23-o)
The pharmaceutical composition according to any one of (18) to (22), wherein the daily dose of the active ingredient of the pharmaceutical composition is 100 mg.
(23-p)
The pharmaceutical composition according to any one of (18) to (22), wherein the daily dose of the active ingredient of the pharmaceutical composition is 70 mg.
(23-q)
The pharmaceutical composition according to any one of (18) to (22), wherein the daily dose of the active ingredient of the pharmaceutical composition is 50 mg.
(23-r)
The pharmaceutical composition according to any one of (18) to (22), wherein the daily dose of the active ingredient of the pharmaceutical composition is 30 mg.
(23-s)
The pharmaceutical composition according to any one of (18) to (22), wherein the daily dose of the active ingredient of the pharmaceutical composition is 20 mg.

(23-t)

The pharmaceutical composition according to any one of (18) to (22), wherein the daily dose of the active ingredient of the pharmaceutical composition is 10 mg.

(24)

The pharmaceutical composition according to any one of (18) to (23), (23-a) to (23-t) and (23-n'), which is administered once daily.

(24B)

The pharmaceutical composition according to any one of (18) to (23), (23-a) to (23-t) and (23-n'), which is administered once daily after a meal.

(24C)

The pharmaceutical composition according to any one of (18) to (23), (23-a) to (23-t) and (23-n'), which is administered once daily at bedtime.

(24D)

The pharmaceutical composition according to any one of (18) to (23), (23-a) to (23-t) and (23-n'), which is administered once daily before a meal.

(24E)

The pharmaceutical composition according to any one of (18) to (23), (23-a) to (23-t) and (23-n'), which is administered once daily between meals.

(25)

A pharmaceutical composition for use in the treatment of chronic cough, which reduces taste disturbance, a side effect related to the treatment, compared to other therapeutic agents for chronic cough.

(26)

The pharmaceutical composition according to (25), wherein the other therapeutic agent for chronic cough is Gefapixant.

(27)

The pharmaceutical composition according to (25), wherein the other therapeutic agent for chronic cough is BAY-1817080.

(28)

The pharmaceutical composition according to (25), wherein the other therapeutic agent for chronic cough is BAY-1902607.

(29)

The pharmaceutical composition according to any one of (25) to (28), comprising a compound or a pharmaceutically acceptable salt thereof having 200-fold or more selectivity for a human $P2X_3$ receptor inhibitory activity over a human $P2X_{2/3}$ receptor inhibitory activity.

The above cough includes daytime cough and/or nighttime cough, regardless of the duration of the cough symptoms. Furthermore, cough includes wet cough and dry cough.

In one embodiment, the chronic cough described above includes idiopathic (unexplained) or treatment-resistant cough.

In one embodiment, the chronic cough described above includes refractory, unexplained and idiopathic cough.

One embodiment includes a pharmaceutical composition for the treatment of chronic cough, in which the side effects of taste disturbance by the administration of the compound represented by Formula (I) or a pharmaceutically acceptable salt thereof are substantially reduced.

One embodiment includes a pharmaceutical composition for treating chronic cough, comprising the compound represented by Formula (I) or a pharmaceutically acceptable salt thereof, wherein the number of chronic coughs is reduced by about 31%.

One embodiment includes a pharmaceutical composition for treating chronic cough, comprising the compound represented by Formula (I) or a pharmaceutically acceptable salt thereof, wherein the cough is a 24-hour cough.

One embodiment includes a pharmaceutical composition for treating chronic cough, comprising the compound represented by Formula (I) or a pharmaceutically acceptable salt thereof, wherein the number of chronic coughs is reduced by about 32%.

One embodiment includes a pharmaceutical composition for treating chronic cough, comprising the compound represented by Formula (I) or a pharmaceutically acceptable salt thereof, wherein the cough is a daytime cough.

One embodiment includes a pharmaceutical composition for treating chronic cough, comprising the compound represented by Formula (I) or a pharmaceutically acceptable salt thereof, wherein the cough is a nighttime cough.

One embodiment includes a method for treating chronic cough, comprising a step of administering an effective amount of the compound represented by Formula (I) or a pharmaceutically acceptable salt thereof to an individual in need of treatment of chronic cough, wherein the number of chronic coughs is reduced by about 31%.

One embodiment includes a method for treating chronic cough, comprising a step of administering an effective amount of the compound represented by Formula (I) or a pharmaceutically acceptable salt thereof to an individual in need of treatment of chronic cough, wherein the cough is a 24-hour cough.

One embodiment includes a method for treating chronic cough, comprising a step of administering an effective amount of the compound represented by Formula (I) or a pharmaceutically acceptable salt thereof to an individual in need of treatment of chronic cough, wherein the number of chronic coughs is reduced by about 32%.

One embodiment includes a method for treating chronic cough, comprising a step of administering an effective amount of the compound represented by Formula (I) or a pharmaceutically acceptable salt thereof to an individual in need of treatment of chronic cough, wherein the cough is a daytime cough.

One embodiment includes a method for treating chronic cough, comprising a step of administering an effective amount of the compound represented by Formula (I) or a pharmaceutically acceptable salt thereof to an individual in need of treatment of chronic cough, wherein the cough is a nighttime cough.

One embodiment includes use of the compound represented by Formula (I) or a pharmaceutically acceptable salt thereof, wherein the number of chronic coughs is reduced by about 31%.

One embodiment includes use of the compound represented by Formula (I) or a pharmaceutically acceptable salt thereof, wherein the cough is a 24-hour cough.

One embodiment includes use of the compound represented by Formula (I) or a pharmaceutically acceptable salt thereof, wherein the number of chronic coughs is reduced by about 32%.

One embodiment includes use of the compound represented by Formula (I) or a pharmaceutically acceptable salt thereof, wherein the cough is a daytime cough.

One embodiment includes use of the compound represented by Formula (I) or a pharmaceutically acceptable salt thereof, wherein the cough is a nighttime cough.

As one embodiment, a pharmaceutical composition for the treatment of chronic cough, comprising 150 mg of the compound represented by Formula (I) or a pharmaceutically acceptable salt thereof, and having substantially no side effects of taste disturbance.

As one embodiment, a method for treating chronic cough, wherein 150 mg of the compound represented by Formula (I) or a pharmaceutically acceptable salt thereof is administered, and having substantially no side effects of taste disturbance.

As one embodiment, use of the compound represented by Formula (I) or a pharmaceutically acceptable salt thereof, wherein 150 mg of the compound represented by Formula (I) or a pharmaceutically acceptable salt thereof is administered, and having substantially no side effects of taste disturbance.

As one embodiment, a pharmaceutical composition for the treatment of chronic cough, comprising 50 mg of the compound represented by Formula (I) or a pharmaceutically acceptable salt thereof, and having substantially no side effects of taste disturbance.

As one embodiment, a method for treating chronic cough, wherein 50 mg of the compound represented by Formula (I) or a pharmaceutically acceptable salt thereof is administered, and having substantially no side effects of taste disturbance.

As one embodiment, use of the compound represented by Formula (I) or a pharmaceutically acceptable salt thereof, wherein 50 mg of the compound represented by Formula (I) or a pharmaceutically acceptable salt thereof is administered, and having substantially no side effects of taste disturbance.

As one embodiment, a pharmaceutical composition for the treatment of chronic cough, comprising 300 mg of the compound represented by Formula (I) or a pharmaceutically acceptable salt thereof, and having substantially no side effects of taste disturbance.

As one embodiment, a method for treating chronic cough, wherein 300 mg of the compound represented by Formula (I) or a pharmaceutically acceptable salt thereof is administered, and having substantially no side effects of taste disturbance.

As one embodiment, use of the compound represented by Formula (I) or a pharmaceutically acceptable salt thereof, wherein 300 mg of the compound represented by Formula (I) or a pharmaceutically acceptable salt thereof is administered, and having substantially no side effects of taste disturbance.

The present invention also relates to the following (101) to (104), (104-a) to (104-t), (104-n'), (104A) to (104E), (105) to (108), (108-a) to (108-t), (108-n'), (108A) to (108E), (109) to (112), (112-a) to (112-t), (112-n'), (112A) to (112E), (113) to (116), (116-a) to (116-t), (116-n'), and (116A) to (116E).

(101)
A pharmaceutical composition for treating acute cough, comprising a compound represented by

[Chemical Formula 5]

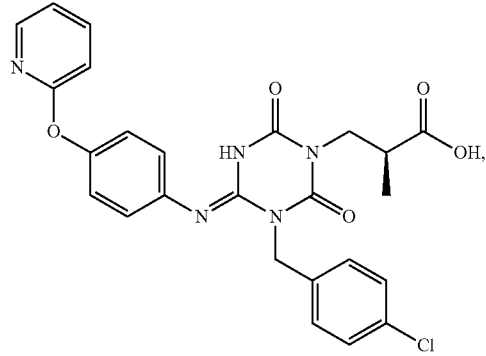

or a pharmaceutically acceptable salt thereof.
(102)
The pharmaceutical composition according to (101), wherein the acute cough is a refractory acute cough.
(103)
The pharmaceutical composition according to (101) or (102), which has substantially no side effects of taste disturbance by the administration of the pharmaceutical composition.
(104)
The pharmaceutical composition according to any one of (101) to (103), wherein the daily dose of the active ingredient of the pharmaceutical composition is 10 mg to 450 mg.
(104-a)
The pharmaceutical composition according to any one of (101) to (103), wherein the daily dose of the active ingredient of the pharmaceutical composition is 10 mg to 300 mg.
(104-b)
The pharmaceutical composition according to any one of (101) to (103), wherein the daily dose of the active ingredient of the pharmaceutical composition is 20 mg to 300 mg.
(104-c)
The pharmaceutical composition according to any one of (101) to (103), wherein the daily dose of the active ingredient of the pharmaceutical composition is 30 mg to 300 mg.
(104-d)
The pharmaceutical composition according to any one of (101) to (103), wherein the daily dose of the active ingredient of the pharmaceutical composition is 50 mg to 300 mg.
(104-e)
The pharmaceutical composition according to any one of (101) to (103), wherein the daily dose of the active ingredient of the pharmaceutical composition is 70 mg to 300 mg.
(104-f)
The pharmaceutical composition according to any one of (101) to (103), wherein the daily dose of the active ingredient of the pharmaceutical composition is 100 mg to 300 mg.
(104-g)
The pharmaceutical composition according to any one of (101) to (103), wherein the daily dose of the active ingredient of the pharmaceutical composition is 150 mg to 300 mg.

(104-h)

The pharmaceutical composition according to any one of (101) to (103), wherein the daily dose of the active ingredient of the pharmaceutical composition is 10 mg to 150 mg.

(104-i)

The pharmaceutical composition according to any one of (101) to (103), wherein the daily dose of the active ingredient of the pharmaceutical composition is 20 mg to 150 mg.

(104-j)

The pharmaceutical composition according to any one of (101) to (103), wherein the daily dose of the active ingredient of the pharmaceutical composition is 30 mg to 150 mg.

(104-k)

The pharmaceutical composition according to any one of (101) to (103), wherein the daily dose of the active ingredient of the pharmaceutical composition is 50 mg to 150 mg.

(104-l)

The pharmaceutical composition according to any one of (101) to (103), wherein the daily dose of the active ingredient of the pharmaceutical composition is 70 mg to 150 mg.

(104-m)

The pharmaceutical composition according to any one of (101) to (103), wherein the daily dose of the active ingredient of the pharmaceutical composition is 100 mg to 150 mg.

(104-n')

The pharmaceutical composition according to any one of (1) to (3), wherein the daily dose of the active ingredient of the pharmaceutical composition is 300 mg.

(104-n)

The pharmaceutical composition according to any one of (101) to (103), wherein the daily dose of the active ingredient of the pharmaceutical composition is 150 mg.

(104-o)

The pharmaceutical composition according to any one of (101) to (103), wherein the daily dose of the active ingredient of the pharmaceutical composition is 100 mg.

(104-p)

The pharmaceutical composition according to any one of (101) to (103), wherein the daily dose of the active ingredient of the pharmaceutical composition is 70 mg.

(104-q)

The pharmaceutical composition according to any one of (101) to (103), wherein the daily dose of the active ingredient of the pharmaceutical composition is 50 mg.

(104-r)

The pharmaceutical composition according to any one of (101) to (103), wherein the daily dose of the active ingredient of the pharmaceutical composition is 30 mg.

(104-s)

The pharmaceutical composition according to any one of (101) to (103), wherein the daily dose of the active ingredient of the pharmaceutical composition is 20 mg.

(104-t)

The pharmaceutical composition according to any one of (101) to (103), wherein the daily dose of the active ingredient of the pharmaceutical composition is 10 mg.

(104A)

The pharmaceutical composition according to any one of (101) to (104), (104-a) to (104-t) and (104-n'), which is administered once daily.

(104B)

The pharmaceutical composition according to any one of (101) to (104), (104-a) to (104-t) and (104-n'), which is administered once daily after a meal.

(104C)

The pharmaceutical composition according to any one of (101) to (104), (104-a) to (104-t) and (104-n'), which is administered once daily at bedtime.

(104D)

The pharmaceutical composition according to any one of (101) to (104), (104-a) to (104-t) and (104-n'), which is administered once daily before a meal.

(104E)

The pharmaceutical composition according to any one of (101) to (104), (104-a) to (104-t) and (104-n'), which is administered once daily between meals.

(105)

A method for treating acute cough, the method comprising a step of administering an effective amount of the compound represented by Formula (I):

[Chemical Formula 6]

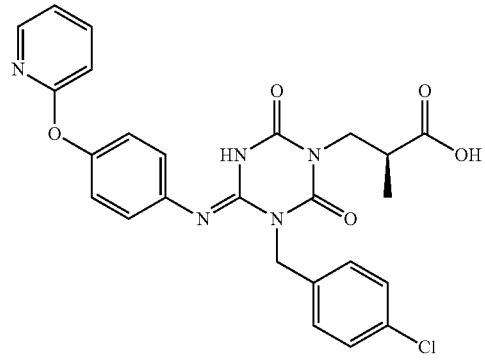

or a pharmaceutically acceptable salt thereof to an individual in need of treatment of acute cough.

(106)

The method of treatment according to (105), wherein the acute cough is a refractory acute cough.

(107)

The method of treatment according to (105) or (106), which has substantially no side effects of taste disturbance by the administration of the compound represented by Formula (I) or a pharmaceutically acceptable salt thereof.

(108)

The method of treatment according to any one of (105) to (107), wherein the daily dose of the active ingredient is 10 mg to 450 mg.

(108-a)

The method of treatment according to any one of (105) to (107), wherein the daily dose of the active ingredient is 10 mg to 300 mg.

(108-b)

The method of treatment according to any one of (105) to (107), wherein the daily dose of the active ingredient is 20 mg to 300 mg.

(108-c)

The method of treatment according to any one of (105) to (107), wherein the daily dose of the active ingredient is 30 mg to 300 mg.

(108-d)

The method of treatment according to any one of (105) to (107), wherein the daily dose of the active ingredient is 50 mg to 300 mg.

(108-e)
The method of treatment according to any one of (105) to (107), wherein the daily dose of the active ingredient is 70 mg to 300 mg.
(108-f)
The method of treatment according to any one of (105) to (107), wherein the daily dose of the active ingredient is 100 mg to 300 mg.
(108-g)
The method of treatment according to any one of (105) to (107), wherein the daily dose of the active ingredient is 150 mg to 300 mg.
(108-h)
The method of treatment according to any one of (105) to (107), wherein the daily dose of the active ingredient is 10 mg to 150 mg.
(108-i)
The method of treatment according to any one of (105) to (107), wherein the daily dose of the active ingredient is 20 mg to 150 mg.
(108-j)
The method of treatment according to any one of (105) to (107), wherein the daily dose of the active ingredient is 30 mg to 150 mg.
(108-k)
The method of treatment according to any one of (105) to (107), wherein the daily dose of the active ingredient is 50 mg to 150 mg.
(108-l)
The method of treatment according to any one of (105) to (107), wherein the daily dose of the active ingredient is 70 mg to 150 mg.
(108-m)
The method of treatment according to any one of (105) to (107), wherein the daily dose of the active ingredient is 100 mg to 150 mg.
(108-n)
The method of treatment according to any one of (105) to (107), wherein the daily dose of the active ingredient is 150 mg.
(108-n')
The method of treatment according to any one of (105) to (107), wherein the daily dose of the active ingredient is 300 mg.
(108-o)
The method of treatment according to any one of (105) to (107), wherein the daily dose of the active ingredient is 100 mg.
(108-p)
The method of treatment according to any one of (105) to (107), wherein the daily dose of the active ingredient is 70 mg.
(108-q)
The method of treatment according to any one of (105) to (107), wherein the daily dose of the active ingredient is 50 mg.
(108-r)
The method of treatment according to any one of (105) to (107), wherein the daily dose of the active ingredient is 30 mg.
(108-s)
The method of treatment according to any one of (105) to (107), wherein the daily dose of the active ingredient is 20 mg.
(108-t)
The method of treatment according to any one of (105) to (107), wherein the daily dose of the active ingredient is 10 mg.
(108A)
The pharmaceutical composition according to any one of (105) to (108), (108-a) to (108-t) and (108-n'), which is administered once daily.
(108B)
The pharmaceutical composition according to any one of (105) to (108), (108-a) to (108-t) and (108-n'), which is administered once daily after a meal.
(108C)
The pharmaceutical composition according to any one of (105) to (108), (108-a) to (108-t) and (108-n'), which is administered once daily at bedtime.
(108D)
The pharmaceutical composition according to any one of (105) to (108), (108-a) to (108-t) and (108-n'), which is administered once daily before a meal.
(108E)
The pharmaceutical composition according to any one of (105) to (108), (108-a) to (108-t) and (108-n'), which is administered once daily between meals.
(109)
Use of a compound represented by Formula (I):

[Chemical Formula 7]

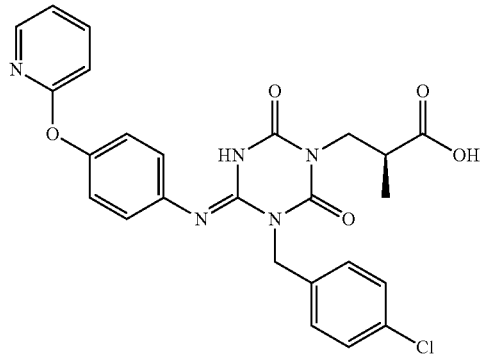

or a pharmaceutically acceptable salt thereof, for the manufacture of a medicament for treating acute cough.
(110)
The use according to (109), wherein the acute cough is a refractory acute cough.
(111)
The use according to (109) or (110), which has substantially no side effects of taste disturbance by the administration of the compound represented by Formula (I) or a pharmaceutically acceptable salt thereof.
(112)
The use according to any one of (109) to (111), wherein the daily dose of the active ingredient is 10 mg to 450 mg.
(112-a)
The use according to any one of (109) to (111), wherein the daily dose of the active ingredient is 10 mg to 300 mg.
(112-b)
The use according to any one of (109) to (111), wherein the daily dose of the active ingredient is 20 mg to 300 mg.
(112-c)
The use according to any one of (109) to (111), wherein the daily dose of the active ingredient is 30 mg to 300 mg.

(112-d)
The use according to any one of (109) to (111), wherein the daily dose of the active ingredient is 50 mg to 300 mg.
(112-e)
The use according to any one of (109) to (111), wherein the daily dose of the active ingredient is 70 mg to 300 mg.
(112-f)
The use according to any one of (109) to (111), wherein the daily dose of the active ingredient is 100 mg to 300 mg.
(112-g)
The use according to any one of (109) to (111), wherein the daily dose of the active ingredient is 150 mg to 300 mg.
(112-h)
The use according to any one of (109) to (111), wherein the daily dose of the active ingredient is 10 mg to 150 mg.
(112-i)
The use according to any one of (109) to (111), wherein the daily dose of the active ingredient is 20 mg to 150 mg.
(112-j)
The use according to any one of (109) to (111), wherein the daily dose of the active ingredient is 30 mg to 150 mg.
(112-k)
The use according to any one of (109) to (111), wherein the daily dose of the active ingredient is 50 mg to 150 mg.
(112-l)
The use according to any one of (109) to (111), wherein the daily dose of the active ingredient is 70 mg to 150 mg.
(112-m)
The use according to any one of (109) to (111), wherein the daily dose of the active ingredient is 100 mg to 150 mg.
(112-n)
The use according to any one of (109) to (111), wherein the daily dose of the active ingredient is 150 mg.
(112-n')
The use according to any one of (109) to (111), wherein the daily dose of the active ingredient is 300 mg.
(112-o)
The use according to any one of (109) to (111), wherein the daily dose of the active ingredient is 100 mg.
(112-p)
The use according to any one of (109) to (111), wherein the daily dose of the active ingredient is 70 mg.
(112-q)
The use according to any one of (109) to (111), wherein the daily dose of the active ingredient is 50 mg.
(112-r)
The use according to any one of (109) to (111), wherein the daily dose of the active ingredient is 30 mg.
(112-s)
The use according to any one of (109) to (111), wherein the daily dose of the active ingredient is 20 mg.
(112-t)
The use according to any one of (109) to (111), wherein the daily dose of the active ingredient is 10 mg.
(112A)
The pharmaceutical composition according to any one of (109) to (112), (112-a) to (112-t) and (112-n'), which is administered once daily.
(112B)
The pharmaceutical composition according to any one of (109) to (112), (112-a) to (112-t) and (112-n'), which is administered once daily after a meal.
(112C)
The pharmaceutical composition according to any one of (109) to (112), (112-a) to (112-t) and (112-n'), which is administered once daily at bedtime.
(112D)
The pharmaceutical composition according to any one of (109) to (112), (112-a) to (112-t) and (112-n'), which is administered once daily before a meal.
(112E)
The pharmaceutical composition according to any one of (109) to (112), (112-a) to (112-t) and (112-n'), which is administered once daily between meals.
(113)
A compound represented by Formula (I):

[Chemical Formula 8]

or a pharmaceutically acceptable salt thereof, for use in the treatment of acute cough.
(114)
The compound according to (113) or a pharmaceutically acceptable salt thereof, wherein the acute cough is a refractory acute cough.
(115)
The compound according to (113) or (114) or a pharmaceutically acceptable salt thereof, which has substantially no side effects of taste disturbance by the administration of the compound represented by Formula (I) or a pharmaceutically acceptable salt thereof.
(116)
The compound according to any one of (113) to (115) or a pharmaceutically acceptable salt thereof, wherein the daily dose of the active ingredient is 10 mg to 450 mg.
(116-a)
The compound according to any one of (113) to (115) or a pharmaceutically acceptable salt thereof, wherein the daily dose of the active ingredient is 10 mg to 300 mg.
(116-b)
The compound according to any one of (113) to (115) or a pharmaceutically acceptable salt thereof, wherein the daily dose of the active ingredient is 20 mg to 300 mg.
(116-c)
The compound according to any one of (113) to (115) or a pharmaceutically acceptable salt thereof, wherein the daily dose of the active ingredient is 30 mg to 300 mg.
(116-d)
The compound according to any one of (113) to (115) or a pharmaceutically acceptable salt thereof, wherein the daily dose of the active ingredient is 50 mg to 300 mg.
(116-e)
The compound according to any one of (113) to (115) or a pharmaceutically acceptable salt thereof, wherein the daily dose of the active ingredient is 70 mg to 300 mg.

(116-f)
The compound according to any one of (113) to (115) or a pharmaceutically acceptable salt thereof, wherein the daily dose of the active ingredient is 100 mg to 300 mg.
(116-g)
The compound according to any one of (113) to (115) or a pharmaceutically acceptable salt thereof, wherein the daily dose of the active ingredient is 150 mg to 300 mg.
(116-h)
The compound according to any one of (113) to (115) or a pharmaceutically acceptable salt thereof, wherein the daily dose of the active ingredient is 10 mg to 150 mg.
(116-i)
The compound according to any one of (113) to (115) or a pharmaceutically acceptable salt thereof, wherein the daily dose of the active ingredient is 20 mg to 150 mg.
(116-j)
The compound according to any one of (113) to (115) or a pharmaceutically acceptable salt thereof, wherein the daily dose of the active ingredient is 30 mg to 150 mg.
(116-k)
The compound according to any one of (113) to (115) or a pharmaceutically acceptable salt thereof, wherein the daily dose of the active ingredient is 50 mg to 150 mg.
(116-l)
The compound according to any one of (113) to (115) or a pharmaceutically acceptable salt thereof, wherein the daily dose of the active ingredient is 70 mg to 150 mg.
(116-m)
The compound according to any one of (113) to (115) or a pharmaceutically acceptable salt thereof, wherein the daily dose of the active ingredient is 100 mg to 150 mg.
(116-n)
The compound according to any one of (113) to (115) or a pharmaceutically acceptable salt thereof, wherein the daily dose of the active ingredient is 150 mg.
(116-n')
The compound according to any one of (113) to (115) or a pharmaceutically acceptable salt thereof, wherein the daily dose of the active ingredient is 300 mg.
(116-o)
The compound according to any one of (113) to (115) or a pharmaceutically acceptable salt thereof, wherein the daily dose of the active ingredient is 100 mg.
(116-p)
The compound according to any one of (113) to (115) or a pharmaceutically acceptable salt thereof, wherein the daily dose of the active ingredient is 70 mg.
(116-q)
The compound according to any one of (113) to (115) or a pharmaceutically acceptable salt thereof, wherein the daily dose of the active ingredient is 50 mg.
(116-r)
The compound according to any one of (113) to (115) or a pharmaceutically acceptable salt thereof, wherein the daily dose of the active ingredient is 30 mg.
(116-s)
The compound according to any one of (113) to (115) or a pharmaceutically acceptable salt thereof, wherein the daily dose of the active ingredient is 20 mg.
(116-t)
The compound according to any one of (113) to (115) or a pharmaceutically acceptable salt thereof, wherein the daily dose of the active ingredient is 10 mg.

(116A)
The pharmaceutical composition according to any one of (113) to (116), (116-a) to (116-t) and (116-n'), which is administered once daily.
(116B)
The pharmaceutical composition according to any one of (113) to (116), (116-a) to (116-t) and (116-n'), which is administered once daily after a meal.
(116C)
The pharmaceutical composition according to any one of (113) to (116), (116-a) to (116-t) and (116-n'), which is administered once daily at bedtime.
(116D)
The pharmaceutical composition according to any one of (113) to (116), (116-a) to (116-t) and (116-n'), which is administered once daily before a meal.
(116E)
The pharmaceutical composition according to any one of (113) to (116), (116-a) to (116-t) and (116-n'), which is administered once daily between meals.

The above cough includes daytime cough and/or nighttime cough, regardless of the duration of the cough symptoms. Furthermore, cough includes wet cough and dry cough.

In one embodiment, the acute cough described above includes idiopathic (unexplained) or treatment-resistant cough.

In one embodiment, the acute cough described above includes refractory, unexplained and idiopathic cough.

One embodiment includes a pharmaceutical composition, in which the side effects of taste disturbance by the administration of the compound represented by Formula (I) are substantially reduced.

One embodiment includes a pharmaceutical composition for the treatment of acute cough, in which the side effects of taste disturbance by the administration of the compound represented by Formula (I) or a pharmaceutically acceptable salt thereof are substantially reduced.

One embodiment includes a pharmaceutical composition for treating acute cough, comprising the compound represented by Formula (I) or a pharmaceutically acceptable salt thereof, wherein the cough is a 24-hour cough.

One embodiment includes a pharmaceutical composition for treating acute cough, comprising the compound represented by Formula (I) or a pharmaceutically acceptable salt thereof, wherein the cough is a daytime cough.

One embodiment includes a pharmaceutical composition for treating acute cough, comprising the compound represented by Formula (I) or a pharmaceutically acceptable salt thereof, wherein the cough is a nighttime cough.

One embodiment includes a method for treating chronic cough, comprising a step of administering an effective amount of the compound represented by Formula (I) or a pharmaceutically acceptable salt thereof to an individual in need of treatment of acute cough, wherein the cough is a 24-hour cough.

One embodiment includes a method for treating chronic cough, comprising a step of administering an effective amount of the compound represented by Formula (I) or a pharmaceutically acceptable salt thereof to an individual in need of treatment of acute cough, wherein the cough is a daytime cough.

One embodiment includes a method for treating chronic cough, comprising a step of administering an effective amount of the compound represented by Formula (I) or a pharmaceutically acceptable salt thereof to an individual in need of treatment of acute cough, wherein the cough is a nighttime cough.

One embodiment includes use of the compound represented by Formula (I) or a pharmaceutically acceptable salt thereof, wherein the cough is a 24-hour cough.

One embodiment includes use of the compound represented by Formula (I) or a pharmaceutically acceptable salt thereof, wherein the cough is a daytime cough.

One embodiment includes use of the compound represented by Formula (I) or a pharmaceutically acceptable salt thereof, wherein the cough is a nighttime cough.

As one embodiment, a pharmaceutical composition for the treatment of acute cough, comprising 150 mg of the compound represented by Formula (I) or a pharmaceutically acceptable salt thereof, and having substantially no side effects of taste disturbance.

As one embodiment, a method for treating acute cough, wherein 150 mg of the compound represented by Formula (I) or a pharmaceutically acceptable salt thereof is administered, and having substantially no side effects of taste disturbance.

As one embodiment, use of the compound represented by Formula (I) or a pharmaceutically acceptable salt thereof, wherein 150 mg of the compound represented by Formula (I) or a pharmaceutically acceptable salt thereof is administered, and having substantially no side effects of taste disturbance.

As one embodiment, a pharmaceutical composition for the treatment of acute cough, comprising 50 mg of the compound represented by Formula (I) or a pharmaceutically acceptable salt thereof, and having substantially no side effects of taste disturbance.

As one embodiment, a method for treating acute cough, wherein 50 mg of the compound represented by Formula (I) or a pharmaceutically acceptable salt thereof is administered, and having substantially no side effects of taste disturbance.

As one embodiment, use of the compound represented by Formula (I) or a pharmaceutically acceptable salt thereof, wherein 50 mg of the compound represented by Formula (I) or a pharmaceutically acceptable salt thereof is administered, and having substantially no side effects of taste disturbance.

As one embodiment, a pharmaceutical composition for the treatment of acute cough, comprising 300 mg of the compound represented by Formula (I) or a pharmaceutically acceptable salt thereof, and having substantially no side effects of taste disturbance.

As one embodiment, a method for treating acute cough, wherein 300 mg of the compound represented by Formula (I) or a pharmaceutically acceptable salt thereof is administered, and having substantially no side effects of taste disturbance.

As one embodiment, use of the compound represented by Formula (I) or a pharmaceutically acceptable salt thereof, wherein 300 mg of the compound represented by Formula (I) or a pharmaceutically acceptable salt thereof is administered, and having substantially no side effects of taste disturbance.

Furthermore, the present invention relates to the following (1001) to (1004), (1004-a) to (1004-t), (1004-n'), (1004A) to (1004E), (1005) to (1008), (1008-a) to (1008-t), (1008-n'), (1008A) to (1008E), (1009) to (1012), (1012-a) to (1012-t), (1012-n'), (1012A) to (1012E), (1013) to (1016), (1016-a) to (1016-t), (1016-n'), and (1016A) to (1016E).

(1001)

A pharmaceutical composition for treating sub-acute cough, comprising a compound represented by

[Chemical Formula 9]

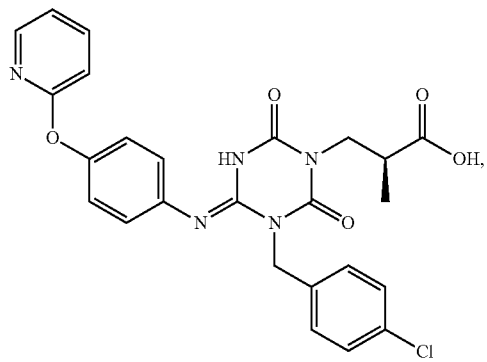

(I)

or a pharmaceutically acceptable salt thereof.

(1002)

The pharmaceutical composition according to (1001), wherein the sub-acute cough is a refractory sub-acute cough.

(1003)

The pharmaceutical composition according to (1001) or (1002), which has substantially no side effects of taste disturbance by the administration of the pharmaceutical composition.

(1004)

The pharmaceutical composition according to any one of (1001) to (1003), wherein the daily dose of the active ingredient of the pharmaceutical composition is 10 mg to 450 mg.

(1004-a)

The pharmaceutical composition according to any one of (1001) to (1003), wherein the daily dose of the active ingredient of the pharmaceutical composition is 10 mg to 300 mg.

(1004-b)

The pharmaceutical composition according to any one of (1001) to (1003), wherein the daily dose of the active ingredient of the pharmaceutical composition is 20 mg to 300 mg.

(1004-c)

The pharmaceutical composition according to any one of (1001) to (1003), wherein the daily dose of the active ingredient of the pharmaceutical composition is 30 mg to 300 mg.

(1004-d)

The pharmaceutical composition according to any one of (1001) to (1003), wherein the daily dose of the active ingredient of the pharmaceutical composition is 50 mg to 300 mg.

(1004-e)

The pharmaceutical composition according to any one of (1001) to (1003), wherein the daily dose of the active ingredient of the pharmaceutical composition is 70 mg to 300 mg.

(1004-f)

The pharmaceutical composition according to any one of (1001) to (1003), wherein the daily dose of the active ingredient of the pharmaceutical composition is 100 mg to 300 mg.

(1004-g)

The pharmaceutical composition according to any one of (1001) to (1003), wherein the daily dose of the active ingredient of the pharmaceutical composition is 150 mg to 300 mg.

(1004-h)

The pharmaceutical composition according to any one of (1001) to (1003), wherein the daily dose of the active ingredient of the pharmaceutical composition is 10 mg to 150 mg.

(1004-i)

The pharmaceutical composition according to any one of (1001) to (1003), wherein the daily dose of the active ingredient of the pharmaceutical composition is 20 mg to 150 mg.

(1004-j)

The pharmaceutical composition according to any one of (1001) to (1003), wherein the daily dose of the active ingredient of the pharmaceutical composition is 30 mg to 150 mg.

(1004-k)

The pharmaceutical composition according to any one of (1001) to (1003), wherein the daily dose of the active ingredient of the pharmaceutical composition is 50 mg to 150 mg.

(1004-l)

The pharmaceutical composition according to any one of (1001) to (1003), wherein the daily dose of the active ingredient of the pharmaceutical composition is 70 mg to 150 mg.

(1004-m)

The pharmaceutical composition according to any one of (1001) to (1003), wherein the daily dose of the active ingredient of the pharmaceutical composition is 100 mg to 150 mg.

(1004-n)

The pharmaceutical composition according to any one of (1001) to (1003), wherein the daily dose of the active ingredient of the pharmaceutical composition is 150 mg.

(1004-n')

The pharmaceutical composition according to any one of (1) to (3), wherein the daily dose of the active ingredient of the pharmaceutical composition is 300 mg.

(1004-o)

The pharmaceutical composition according to any one of (1001) to (1003), wherein the daily dose of the active ingredient of the pharmaceutical composition is 100 mg.

(1004-p)

The pharmaceutical composition according to any one of (1001) to (1003), wherein the daily dose of the active ingredient of the pharmaceutical composition is 70 mg.

(1004-q)

The pharmaceutical composition according to any one of (1001) to (1003), wherein the daily dose of the active ingredient of the pharmaceutical composition is 50 mg.

(1004-r)

The pharmaceutical composition according to any one of (1001) to (1003), wherein the daily dose of the active ingredient of the pharmaceutical composition is 30 mg.

(1004-s)

The pharmaceutical composition according to any one of (1001) to (1003), wherein the daily dose of the active ingredient of the pharmaceutical composition is 20 mg.

(1004-t)

The pharmaceutical composition according to any one of (1001) to (1003), wherein the daily dose of the active ingredient of the pharmaceutical composition is 10 mg.

(1004A)

The pharmaceutical composition according to any one of (1001) to (1004), (1004-a) to (1004-t) and (1004-n'), which is administered once daily.

(1004B)

The pharmaceutical composition according to any one of (1001) to (1004), (1004-a) to (1004-t) and (1004-n'), which is administered once daily after a meal.

(1004C)

The pharmaceutical composition according to any one of (1001) to (1004), (1004-a) to (1004-t) and (1004-n'), which is administered once daily at bedtime.

(1004D)

The pharmaceutical composition according to any one of (1001) to (1004), (1004-a) to (1004-t) and (1004-n'), which is administered once daily before a meal.

(1004E)

The pharmaceutical composition according to any one of (1001) to (1004), (1004-a) to (1004-t) and (1004-n'), which is administered once daily between meals.

(1005)

A method for treating sub-acute cough, the method comprising a step of administering an effective amount of a compound represented by Formula (I):

[Chemical Formula 10]

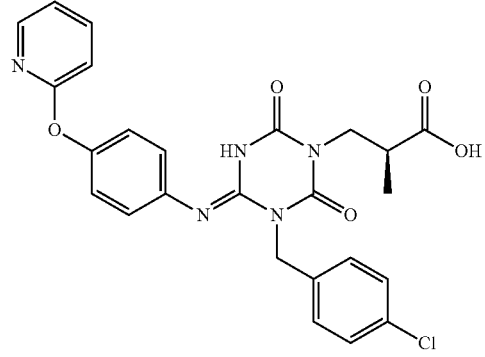

(I)

or a pharmaceutically acceptable salt thereof to an individual in need of treatment of sub-acute cough.

(1006)

The method of treatment according to (1005), wherein the sub-acute cough is a refractory sub-acute cough.

(1007)

The method of treatment according to (1005) or (1006), which has substantially no side effects of taste disturbance by the administration of the compound represented by Formula (I) or a pharmaceutically acceptable salt thereof.

(1008)

The method of treatment according to any one of (1005) to (1007), wherein the daily dose of the active ingredient is 10 mg to 450 mg.

(1008-a)

The method of treatment according to any one of (1005) to (1007), wherein the daily dose of the active ingredient is 10 mg to 300 mg.

(1008-b)

The method of treatment according to any one of (1005) to (1007), wherein the daily dose of the active ingredient is 20 mg to 300 mg.

(1008-c)

The method of treatment according to any one of (1005) to (1007), wherein the daily dose of the active ingredient is 30 mg to 300 mg.

(1008-d)
The method of treatment according to any one of (1005) to (1007), wherein the daily dose of the active ingredient is 50 mg to 300 mg.
(1008-e)
The method of treatment according to any one of (1005) to (1007), wherein the daily dose of the active ingredient is 70 mg to 300 mg.
(1008-f)
The method of treatment according to any one of (1005) to (1007), wherein the daily dose of the active ingredient is 100 mg to 300 mg.
(1008-g)
The method of treatment according to any one of (1005) to (1007), wherein the daily dose of the active ingredient is 150 mg to 300 mg.
(1008-h)
The method of treatment according to any one of (1005) to (1007), wherein the daily dose of the active ingredient is 10 mg to 150 mg.
(1008-i)
The method of treatment according to any one of (1005) to (1007), wherein the daily dose of the active ingredient is 20 mg to 150 mg.
(1008-j)
The method of treatment according to any one of (1005) to (1007), wherein the daily dose of the active ingredient is 30 mg to 150 mg.
(1008-k)
The method of treatment according to any one of (1005) to (1007), wherein the daily dose of the active ingredient is 50 mg to 150 mg.
(1008-l)
The method of treatment according to any one of (1005) to (1007), wherein the daily dose of the active ingredient is 70 mg to 150 mg.
(1008-m)
The method of treatment according to any one of (1005) to (1007), wherein the daily dose of the active ingredient is 100 mg to 150 mg.
(1008-n)
The method of treatment according to any one of (1005) to (1007), wherein the daily dose of the active ingredient is 150 mg.
(1008-n')
The method of treatment according to any one of (1005) to (1007), wherein the daily dose of the active ingredient is 300 mg.
(1008-o)
The method of treatment according to any one of (1005) to (1007), wherein the daily dose of the active ingredient is 100 mg.
(1008-p)
The method of treatment according to any one of (1005) to (1007), wherein the daily dose of the active ingredient is 70 mg.
(1008-q)
The method of treatment according to any one of (1005) to (1007), wherein the daily dose of the active ingredient is 50 mg.
(1008-r)
The method of treatment according to any one of (1005) to (1007), wherein the daily dose of the active ingredient is 30 mg.
(1008-s)
The method of treatment according to any one of (1005) to (1007), wherein the daily dose of the active ingredient is 20 mg.
(1008-t)
The method of treatment according to any one of (1005) to (1007), wherein the daily dose of the active ingredient is 10 mg.
(1008A)
The pharmaceutical composition according to any one of (1005) to (1008), (1008-a) to (1008-t) and (1008-n'), which is administered once daily.
(1008B)
The pharmaceutical composition according to any one of (1005) to (1008), (1008-a) to (1008-t) and (1008-n'), which is administered once daily after a meal.
(1008C)
The pharmaceutical composition according to any one of (1005) to (1008), (1008-a) to (1008-t) and (1008-n'), which is administered once daily at bedtime.
(1008D)
The pharmaceutical composition according to any one of (1005) to (1008), (1008-a) to (1008-t) and (1008-n'), which is administered once daily before a meal.
(1008E)
The pharmaceutical composition according to any one of (1005) to (1008), (1008-a) to (1008-t) and (1008-n'), which is administered once daily between meals.
(1009)
Use of a compound represented by Formula (I):

[Chemical Formula 11]

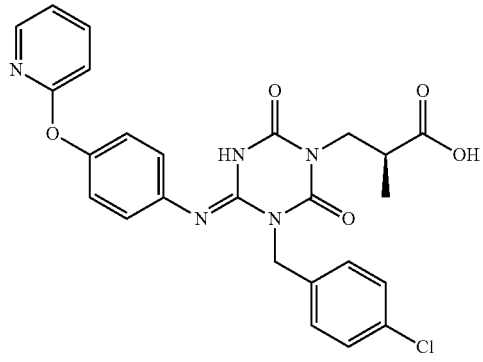

or a pharmaceutically acceptable salt thereof, for the manufacture of a medicament for treating sub-acute cough.
(1010)
The use according to (1009), wherein the sub-acute cough is a refractory sub-acute cough.
(1011)
The use according to (1009) or (1010), which has substantially no side effects of taste disturbance by the administration of the compound represented by Formula (I) or a pharmaceutically acceptable salt thereof.
(1012)
The use according to any one of (1009) to (1011), wherein the daily dose of the active ingredient is 10 mg to 450 mg.
(1012-a)
The use according to any one of (1009) to (1011), wherein the daily dose of the active ingredient is 10 mg to 300 mg.

(1012-b)
The use according to any one of (1009) to (1011), wherein the daily dose of the active ingredient is 20 mg to 300 mg.
(1012-c)
The use according to any one of (1009) to (1011), wherein the daily dose of the active ingredient is 30 mg to 300 mg.
(1012-d)
The use according to any one of (1009) to (1011), wherein the daily dose of the active ingredient is 50 mg to 300 mg.
(1012-e)
The use according to any one of (1009) to (1011), wherein the daily dose of the active ingredient is 70 mg to 300 mg.
(1012-f)
The use according to any one of (1009) to (1011), wherein the daily dose of the active ingredient is 100 mg to 300 mg.
(1012-g)
The use according to any one of (1009) to (1011), wherein the daily dose of the active ingredient is 150 mg to 300 mg.
(1012-h)
The use according to any one of (1009) to (1011), wherein the daily dose of the active ingredient is 10 mg to 150 mg.
(1012-i)
The use according to any one of (1009) to (1011), wherein the daily dose of the active ingredient is 20 mg to 150 mg.
(1012-j)
The use according to any one of (1009) to (1011), wherein the daily dose of the active ingredient is 30 mg to 150 mg.
(1012-k)
The use according to any one of (1009) to (1011), wherein the daily dose of the active ingredient is 50 mg to 150 mg.
(1012-l)
The use according to any one of (1009) to (1011), wherein the daily dose of the active ingredient is 70 mg to 150 mg.
(1012-m)
The use according to any one of (1009) to (1011), wherein the daily dose of the active ingredient is 100 mg to 150 mg.
(1012-n)
The use according to any one of (1009) to (1011), wherein the daily dose of the active ingredient is 150 mg.
(1012-n')
The use according to any one of (1009) to (1011), wherein the daily dose of the active ingredient is 300 mg.
(1012-o)
The use according to any one of (1009) to (1011), wherein the daily dose of the active ingredient is 100 mg.
(1012-p)
The use according to any one of (1009) to (1011), wherein the daily dose of the active ingredient is 70 mg.
(1012-q)
The use according to any one of (1009) to (1011), wherein the daily dose of the active ingredient is 50 mg.
(1012-r)
The use according to any one of (1009) to (1011), wherein the daily dose of the active ingredient is 30 mg.
(1012-s)
The use according to any one of (1009) to (1011), wherein the daily dose of the active ingredient is 20 mg.
(1012-t)
The use according to any one of (1009) to (1011), wherein the daily dose of the active ingredient is 10 mg.
(1012A)
The pharmaceutical composition according to any one of (1009) to (1012), (1012-a) to (1012-t) and (1012-n'), which is administered once daily.

(1012B)
The pharmaceutical composition according to any one of (1009) to (1012), (1012-a) to (1012-t) and (1012-n'), which is administered once daily after a meal.
(1012C)
The pharmaceutical composition according to any one of (1009) to (1012), (1012-a) to (1012-t) and (1012-n'), which is administered once daily at bedtime.
(1012D)
The pharmaceutical composition according to any one of (1009) to (1012), (1012-a) to (1012-t) and (1012-n'), which is administered once daily before a meal.
(1012E)
The pharmaceutical composition according to any one of (1009) to (1012), (1012-a) to (1012-t) and (1012-n'), which is administered once daily between meals.
(1013)
A compound represented by Formula (I):

[Chemical Formula 12]

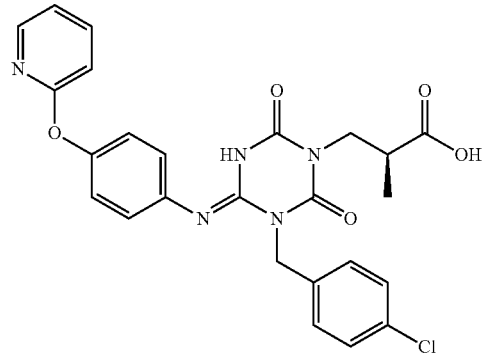

or a pharmaceutically acceptable salt thereof, for use in the treatment of sub-acute cough.
(1014)
The compound according to (1013) or a pharmaceutically acceptable salt thereof, wherein the sub-acute cough is a refractory sub-acute cough.
(1015)
The compound according to (1013) or (1014) or a pharmaceutically acceptable salt thereof, which has substantially no side effects of taste disturbance by the administration of the compound represented by Formula (I) or a pharmaceutically acceptable salt thereof.
(1016)
The compound according to any one of (1013) to (1015) or a pharmaceutically acceptable salt thereof, wherein the daily dose of the active ingredient is 10 mg to 450 mg.
(1016-a)
The compound according to any one of (1013) to (1015) or a pharmaceutically acceptable salt thereof, wherein the daily dose of the active ingredient is 10 mg to 300 mg.
(1016-b)
The compound according to any one of (1013) to (1015) or a pharmaceutically acceptable salt thereof, wherein the daily dose of the active ingredient is 20 mg to 300 mg.
(1016-c)
The compound according to any one of (1013) to (1015) or a pharmaceutically acceptable salt thereof, wherein the daily dose of the active ingredient is 30 mg to 300 mg.

(1016-d)
The compound according to any one of (1013) to (1015) or a pharmaceutically acceptable salt thereof, wherein the daily dose of the active ingredient is 50 mg to 300 mg.
(1016-e)
The compound according to any one of (1013) to (1015) or a pharmaceutically acceptable salt thereof, wherein the daily dose of the active ingredient is 70 mg to 300 mg.
(1016-f)
The compound according to any one of (1013) to (1015) or a pharmaceutically acceptable salt thereof, wherein the daily dose of the active ingredient is 100 mg to 300 mg.
(1016-g)
The compound according to any one of (1013) to (1015) or a pharmaceutically acceptable salt thereof, wherein the daily dose of the active ingredient is 150 mg to 300 mg.
(1016-h)
The compound according to any one of (1013) to (1015) or a pharmaceutically acceptable salt thereof, wherein the daily dose of the active ingredient is 10 mg to 150 mg.
(1016-i)
The compound according to any one of (1013) to (1015) or a pharmaceutically acceptable salt thereof, wherein the daily dose of the active ingredient is 20 mg to 150 mg.
(1016-j)
The compound according to any one of (1013) to (1015) or a pharmaceutically acceptable salt thereof, wherein the daily dose of the active ingredient is 30 mg to 150 mg.
(1016-k)
The compound according to any one of (1013) to (1015) or a pharmaceutically acceptable salt thereof, wherein the daily dose of the active ingredient is 50 mg to 150 mg.
(1016-l)
The compound according to any one of (1013) to (1015) or a pharmaceutically acceptable salt thereof, wherein the daily dose of the active ingredient is 70 mg to 150 mg.
(1016-m)
The compound according to any one of (1013) to (1015) or a pharmaceutically acceptable salt thereof, wherein the daily dose of the active ingredient is 100 mg to 150 mg.
(1016-n)
The compound according to any one of (1013) to (1015) or a pharmaceutically acceptable salt thereof, wherein the daily dose of the active ingredient is 150 mg.
(1016-n')
The compound according to any one of (1013) to (1015) or a pharmaceutically acceptable salt thereof, wherein the daily dose of the active ingredient is 300 mg.
(1016-o)
The compound according to any one of (1013) to (1015) or a pharmaceutically acceptable salt thereof, wherein the daily dose of the active ingredient is 100 mg.
(1016-p)
The compound according to any one of (1013) to (1015) or a pharmaceutically acceptable salt thereof, wherein the daily dose of the active ingredient is 70 mg.
(1016-q)
The compound according to any one of (1013) to (1015) or a pharmaceutically acceptable salt thereof, wherein the daily dose of the active ingredient is 50 mg.
(1016-r)
The compound according to any one of (1013) to (1015) or a pharmaceutically acceptable salt thereof, wherein the daily dose of the active ingredient is 30 mg.
(1016-s)
The compound according to any one of (1013) to (1015) or a pharmaceutically acceptable salt thereof, wherein the daily dose of the active ingredient is 20 mg.
(1016-t)
The compound according to any one of (1013) to (1015) or a pharmaceutically acceptable salt thereof, wherein the daily dose of the active ingredient is 10 mg.
(1016A)
The pharmaceutical composition according to any one of (1013) to (1016), (1016-a) to (1016-t) and (1016-n'), which is administered once daily.
(1016B)
The pharmaceutical composition according to any one of (1013) to (1016), (1016-a) to (1016-t) and (1016-n'), which is administered once daily after a meal.
(1016C)
The pharmaceutical composition according to any one of (1013) to (1016), (1016-a) to (1016-t) and (1016-n'), which is administered once daily at bedtime.
(1016D)
The pharmaceutical composition according to any one of (1013) to (1016), (1016-a) to (1016-t) and (1016-n'), which is administered once daily before a meal.
(1016E)
The pharmaceutical composition according to any one of (1013) to (1016), (1016-a) to (1016-t) and (1016-n'), which is administered once daily between meals.

The above cough includes daytime cough and/or nighttime cough, regardless of the duration of the cough symptoms. Furthermore, cough includes wet cough and dry cough.

In one embodiment, the sub-acute cough described above includes idiopathic (unexplained) or treatment-resistant cough.

In one embodiment, the sub-acute cough described above includes refractory, unexplained and idiopathic cough.

One embodiment includes a pharmaceutical composition, wherein the side effects of taste disturbance by the administration of the compound represented by Formula (I) are substantially reduced.

One embodiment includes a pharmaceutical composition for the treatment of sub-acute cough, in which the side effects of taste disturbance by the administration of the compound represented by Formula (I) or a pharmaceutically acceptable salt thereof are substantially reduced.

One embodiment includes a pharmaceutical composition for treating sub-acute cough, comprising the compound represented by Formula (I) or a pharmaceutically acceptable salt thereof, wherein the cough is a 24-hour cough.

One embodiment includes a pharmaceutical composition for treating sub-acute cough, comprising the compound represented by Formula (I) or a pharmaceutically acceptable salt thereof, wherein the cough is a daytime cough.

One embodiment includes a pharmaceutical composition for treating sub-acute cough, comprising the compound represented by Formula (I) or a pharmaceutically acceptable salt thereof, wherein the cough is a nighttime cough.

One embodiment includes a method for treating chronic cough, comprising a step of administering an effective amount of the compound represented by Formula (I) or a pharmaceutically acceptable salt thereof to an individual in need of treatment of sub-acute cough, wherein the cough is a 24-hour cough.

One embodiment includes a method for treating chronic cough, comprising a step of administering an effective amount of the compound represented by Formula (I) or a pharmaceutically acceptable salt thereof to an individual in need of treatment of sub-acute cough, wherein the cough is a daytime cough.

One embodiment includes a method for treating chronic cough, comprising a step of administering an effective amount of the compound represented by Formula (I) or a pharmaceutically acceptable salt thereof to an individual in need of treatment of sub-acute cough, wherein the cough is a nighttime cough.

One embodiment includes use of the compound represented by Formula (I) or a pharmaceutically acceptable salt thereof, wherein the cough is a 24-hour cough.

One embodiment includes use of the compound represented by Formula (I) or a pharmaceutically acceptable salt thereof, wherein the cough is a daytime cough.

One embodiment includes use of the compound represented by Formula (I) or a pharmaceutically acceptable salt thereof, wherein the cough is a nighttime cough.

As one embodiment, a pharmaceutical composition for the treatment of sub-acute cough, comprising 150 mg of the compound represented by Formula (I) or a pharmaceutically acceptable salt thereof, and having substantially no side effects of taste disturbance.

As one embodiment, a method for treating sub-acute cough, wherein 150 mg of the compound represented by Formula (I) or a pharmaceutically acceptable salt thereof is administered, and having substantially no side effects of taste disturbance.

As one embodiment, use of the compound represented by Formula (I) or a pharmaceutically acceptable salt thereof, wherein 150 mg of the compound represented by Formula (I) or a pharmaceutically acceptable salt thereof is administered, and having substantially no side effects of taste disturbance.

As one embodiment, a pharmaceutical composition for the treatment of sub-acute cough, comprising 50 mg of the compound represented by Formula (I) or a pharmaceutically acceptable salt thereof, and having substantially no side effects of taste disturbance.

As one embodiment, a method for treating sub-acute cough, wherein 50 mg of the compound represented by Formula (I) or a pharmaceutically acceptable salt thereof is administered, and having substantially no side effects of taste disturbance.

As one embodiment, use of the compound represented by Formula (I) or a pharmaceutically acceptable salt thereof, wherein 50 mg of the compound represented by Formula (I) or a pharmaceutically acceptable salt thereof is administered, and having substantially no side effects of taste disturbance.

As one embodiment, a pharmaceutical composition for the treatment of sub-acute cough, comprising 300 mg of the compound represented by Formula (I) or a pharmaceutically acceptable salt thereof, and having substantially no side effects of taste disturbance.

As one embodiment, a method for treating sub-acute cough, wherein 300 mg of the compound represented by Formula (I) or a pharmaceutically acceptable salt thereof is administered, and having substantially no side effects of taste disturbance.

As one embodiment, use of the compound represented by Formula (I) or a pharmaceutically acceptable salt thereof, wherein 300 mg of the compound represented by Formula (I) or a pharmaceutically acceptable salt thereof is administered, and having substantially no side effects of taste disturbance.

Effect of the Invention

The compound represented by Formula (I) of the present invention has an excellent effect of being effective in the treatment of chronic cough. In addition, the compound represented by Formula (I) is a highly safe drug having substantially no taste-related side effects, or reduced side effects of taste disturbance.

BRIEF DESCRIPTION OF DRAWING

FIG. 1 represents a plot (largest analysis population) of the changes in daytime cough frequency (per hour) in patients with chronic cough.

MODE FOR CARRYING OUT THE INVENTION

The term "consist of" means having only components. The term "comprise" means not restricting with components and not excluding undescribed factors.

Hereinafter, the present invention will be described with reference to embodiments. Throughout the present description, an expression in the singular form should be understood as also including the concept of its plural form, unless otherwise stated. Therefore, the singular articles (for example, "a", "an", "the", and the like in English) should be understood as also including the concept of their plural form, unless otherwise stated.

In addition, the terms used in the present description should be understood as being used in the meaning commonly used in the art unless otherwise stated. Therefore, unless otherwise defined, all terminology and scientific terms used in the present description have the same meaning as commonly understood by those skilled in the art to which the present invention belongs. In case of conflict, the present description (including definitions) prevails.

The pharmaceutical composition for treating chronic cough of the present invention is characterized by being a pharmaceutical composition containing a compound represented by Formula (I):

[Chemical Formula 13]

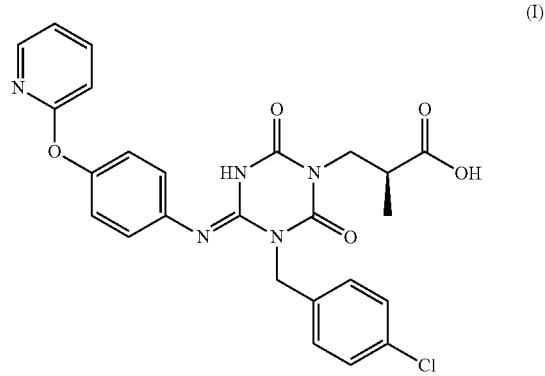 [SMILES: C[C@@H](Cn1c(=O)[nH]/c(=N\c2ccc(Oc3ccccn3)cc2)n(Cc2ccc(Cl)cc2)c1=O)C(=O)O]

or a pharmaceutically acceptable salt thereof, as an active ingredient. In the present description, the pharmaceutical composition for treating chronic cough of the present invention is also referred to as a therapeutic agent for chronic cough.

The compound represented by Formula (I) or a pharmaceutically acceptable salt thereof used in the present invention may be a solvate thereof.

The compound represented by Formula (I) is (2S)-3-(3-[(4-Chlorophenyl)methyl]-2,6-dioxo-4-{[4-(pyridin-2-yloxy)phenyl]amino}-3,6-dihydro-1,3,5-triazin-1(2H)-yl)-2-methyl-propanoic acid, and has $P2X_3$ and/or $P2X_{2/3}$ receptor antagonist activity. In addition, the compound represented by Formula (I) includes the following tautomer.

[Chemical Formula 14]

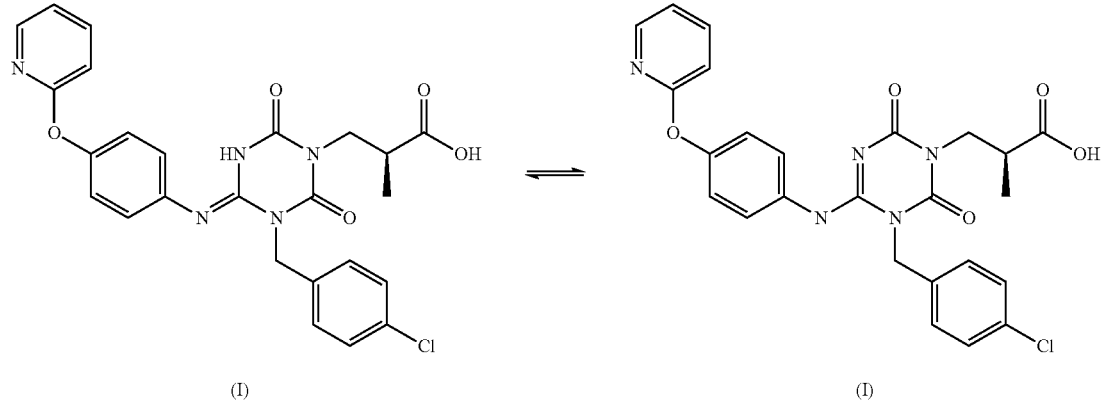

(I)                                         (I)

The compound represented by Formula (I) can be synthesized according to a known method, for example, the methods described in International Publication No. WO 2014/200078 and International Publication No. WO 2012/020749.

In the present description, as the "pharmaceutically acceptable salt", examples of basic salts include alkali metal salts such as lithium salt, sodium salt and potassium salt; alkaline earth metal salts such as calcium salt and barium salt; transition metal salts such as zinc salt and iron salt; magnesium salt; ammonium salt; aliphatic amine salts such as trimethylamine salt, triethylamine salt, dicyclohexylamine salt, ethanolamine salt, diethanolamine salt, triethanolamine salt, ethylenediamine salt, meglumine salt and procaine salt; aralkylamine salts such as N,N-dibenzylethylenediamine; aromatic heterocyclic amine salts such as pyridine salt, picoline salt, quinoline salt and isoquinoline salt; quaternary ammonium salts such as tetramethylammonium salt, tetraethylammonium salt, benzyltrimethylammonium salt, benzyltriethylammonium salt, benzyltributylammonium salt, methyltrioctylammonium salt and tetrabutylammonium salt; and basic amino acid salts such as arginine salt and lysine salt. Examples of acidic salts include inorganic acid salts such as hydrochloride, sulfate, nitrate, phosphate, carbonate, hydrogen carbonate, hydrobromate, hydroiodide and perchlorate; organic acid salts such as formate, acetate, propionate, trifluoroacetate, citrate, lactate, tartrate, oxalate, maleate, fumarate, mandelate, glutarate, malate, benzoate, phthalate and ascorbate; sulfonates such as methanesulfonate, ethanesulfonate, isethionate, benzenesulfonate and p-toluenesulfonate; and acidic amino acid salts such as aspartate and glutamate.

Solvates include organic solvates in which any number of organic solvent molecules are coordinated and hydrates in which any number of water molecules are coordinated. In the present description, the term "solvate" means a solvate of the compound represented by the above Formula (I) or a pharmaceutically acceptable salt thereof, and examples thereof include a monosolvate, a disolvate, a monohydrate and a dihydrate.

Pharmaceutically acceptable salts and solvates can be synthesized according to a known method.

In addition, as other pharmaceutical raw materials, additives such as excipients, binders, disintegrants, lubricants, sweeteners, flavoring agents, preservatives, chelating agents, antioxidants, cooling agents, coating agents, stabilizers, fluidizers, viscous agents, solubilizers, thickeners, buffers, flavors, colorants, adsorbents, wetting agents, moisture-proof agents, antistatic agents, plasticizers, antifoaming agents, surfactants, and emulsifiers may be contained. Specifically, binders (for example, corn starch, and the like), fillers (for example, lactose, microcrystalline cellulose, and the like), disintegrants (for example, sodium starch glycolate, and the like), and lubricants (for example, magnesium stearate, and the like) can be mentioned. Their contents are not limited.

The pharmaceutical composition for the treatment of chronic cough of the present invention can be prepared according to a method known to those skilled in the art. Moreover, the shape and size of the therapeutic agent are not limited. However, oral preparations are preferable, and among these, solid preparations are more preferable. Examples of dosage forms of solid preparations can include tablets (including orally fast disintegrating tablets, chewable tablets, effervescent tablets, jelly drops, and the like), lozenges, granules, pills, powders (including fine granules), and capsules (including hard capsules and soft capsules). Moreover, when preparing these, a coating treatment may be performed by a known method.

The dose of the ingredients when used as a pharmaceutical composition for the treatment of chronic cough depends on the mode of administration, patient symptoms, age, weight, gender, or other concomitant drugs (if any), and is ultimately left to the discretion of the physician. Examples includes an aspect in which a daily adult dose of 10 to 450 mg of the compound represented by Formula (I) or a pharmaceutically acceptable salt thereof is orally administered.

One embodiment includes an aspect in which a daily adult dose of 10 mg to 300 mg of the compound represented by Formula (I) or a pharmaceutically acceptable salt thereof is orally administered.

One embodiment includes an aspect in which a daily adult dose of 20 mg to 300 mg of the compound represented by Formula (I) or a pharmaceutically acceptable salt thereof is orally administered.

One embodiment includes an aspect in which a daily adult dose of 30 mg to 300 mg of the compound represented by Formula (I) or a pharmaceutically acceptable salt thereof is orally administered.

One embodiment includes an aspect in which a daily adult dose of 50 mg to 300 mg of the compound represented by Formula (I) or a pharmaceutically acceptable salt thereof is orally administered.

One embodiment includes an aspect in which a daily adult dose of 70 mg to 300 mg of the compound represented by Formula (I) or a pharmaceutically acceptable salt thereof is orally administered.

One embodiment includes an aspect in which a daily adult dose of 100 mg to 300 mg of the compound represented by Formula (I) or a pharmaceutically acceptable salt thereof is orally administered.

One embodiment includes an aspect in which a daily adult dose of 150 mg to 300 mg of the compound represented by Formula (I) or a pharmaceutically acceptable salt thereof is orally administered.

One embodiment includes an aspect in which a daily adult dose of 10 mg to 150 mg of the compound represented by Formula (I) or a pharmaceutically acceptable salt thereof is orally administered.

One embodiment includes an aspect in which a daily adult dose of 20 mg to 150 mg of the compound represented by Formula (I) or a pharmaceutically acceptable salt thereof is orally administered.

One embodiment includes an aspect in which a daily adult dose of 30 mg to 150 mg of the compound represented by Formula (I) or a pharmaceutically acceptable salt thereof is orally administered.

One embodiment includes an aspect in which a daily adult dose of 50 mg to 150 mg of the compound represented by Formula (I) or a pharmaceutically acceptable salt thereof is orally administered.

One embodiment includes an aspect in which a daily adult dose of 70 mg to 150 mg of the compound represented by Formula (I) or a pharmaceutically acceptable salt thereof is orally administered.

One embodiment includes an aspect in which a daily adult dose of 100 mg to 150 mg of the compound represented by Formula (I) or a pharmaceutically acceptable salt thereof is orally administered.

One embodiment includes an aspect in which a daily adult dose of, for example, 10 mg, 15 mg, 20 mg, 25 mg, 30 mg, 35 mg, 40 mg, 45 mg, 50 mg, 55 mg, 60 mg, 65 mg, 70 mg, 75 mg, 80 mg, 85 mg, 90 mg, 95 mg, 100 mg, 105 mg, 110 mg, 115 mg, 120 mg, 125 mg, 130 mg, 135 mg, 140 mg, 145 mg or 150 mg of the compound represented by Formula (I) or a pharmaceutically acceptable salt thereof is orally administered.

One embodiment includes an aspect in which a daily adult dose of, for example, 150 mg, 200 mg, 250 mg or 300 mg of the compound represented by Formula (I) or a pharmaceutically acceptable salt thereof is orally administered.

The dose may be administered at once or in divided doses. For example, the above dose is administered once a day. For example, the above dose is administered in two divided doses per day. For example, the above dose is administered in three divided doses per day. For example, the above dose is administered in four divided doses per day.

In one embodiment, the symptom, condition or disease of the respiratory tract is attenuated by the compound represented by Formula (I) or a pharmaceutically acceptable salt thereof. The respiratory disease may be selected from many conditions in which cough hypersensitivity is dominant, and can include unexplained cough, or cough associated with upper respiratory tract infection, chronic obstructive pulmonary disease (COPD), asthma, or idiopathic pulmonary fibrosis.

In one embodiment, the cough is a form of refractory cough, unexplained cough, idiopathic cough, sub-acute or chronic cough, treatment-resistant cough, idiopathic chronic cough, postviral cough, iatrogenic cough, cough associated with postnasal drip, cough associated with upper respiratory tract infection, asthma and/or COPD, cough associated with interstitial diseases, cough associated with reflux esophagitis (GERD) and/or cough or bronchitis associated with smoking. Iatrogenic cough can be induced by ACE inhibitors. In addition, the interstitial disease can be pulmonary fibrosis.

In the present description, the term "respiratory disease" includes, but is not limited to, cough hypersensitivity syndrome, chronic obstructive pulmonary disease (COPD), asthma, and bronchospasm. Examples of respiratory diseases include embodiments of refractory cough, unexplained cough, idiopathic cough, sub-acute or chronic cough, treatment-resistant cough, idiopathic chronic cough, cough associated with upper respiratory infection, postviral cough, iatrogenic cough (e.g., ACE inhibitor-induced), cough or bronchitis associated with idiopathic pulmonary fibrosis or smoking. Respiratory diseases include the urge to cough associated with any respiratory disease, for example, the urge to cough associated with chronic obstructive pulmonary disease (COPD), cough variant asthma, or interstitial lung disease, or to wheeze.

In the present description, "acute cough" is interpreted to mean a cough that lasts up to 3 weeks in duration. For example, an acute cough can be the result of an acute illness such as a cold or the flu. The acute cough can disappear when the causative factor (for example, cold or flu) is eliminated.

In the present description, "sub-acute cough" is interpreted to mean a cough that lasts for 3 to 8 weeks. A sub-acute cough follows the period during which a subject is infected with a disease (for example, cold or flu). A sub-acute cough is a cough that often remains after the causative factor has been removed. For example, sub-acute cough appears after an infection (for example, after a viral infection).

In the present description, "chronic cough" refers to a persistent or refractory cough that lasts longer than 8 weeks without any evident causative factor, and may not be associated with other respiratory diseases such as asthma or COPD.

In one embodiment, the present invention includes a method for treating the cough symptoms and urges to cough associated with respiratory diseases by administering the compound represented by Formula (I) or a pharmaceutically acceptable salt thereof.

In one embodiment, the present invention includes a compound for using the compound represented by Formula (I) or a pharmaceutically acceptable salt thereof in the treatment of the cough symptoms and urges to cough associated with respiratory diseases in a subject in need of treatment.

In one embodiment, the present invention includes use of the compound represented by Formula (I) or a pharmaceutically acceptable salt thereof for the manufacture of a medicament for treating the cough symptoms and urges to cough associated with respiratory diseases in a subject in need of treatment.

In one embodiment, the present invention includes a method of treating the chronic cough symptoms and/or urges to cough associated with respiratory diseases or diseases mediated by P2X$_3$ and/or P2X$_{2/3}$ receptor antagonists by administering the compound represented by Formula (I) or a pharmaceutically acceptable salt thereof.

In one embodiment, the present invention includes the compound represented by Formula (I) or a pharmaceutically acceptable salt thereof for use in the treatment of the chronic cough symptoms and/or urges to cough associated with respiratory diseases or diseases mediated by P2X$_3$ and/or P2X$_{2/3}$ receptor antagonists.

In one embodiment, the present invention includes use of the compound represented by Formula (I) or a pharmaceutically acceptable salt thereof for the manufacture of a medicament for treating the chronic cough symptoms and/or urges to cough associated with respiratory diseases or diseases mediated by P2X$_3$ and/or P2X$_{2/3}$ receptor antagonists.

In one embodiment, the present invention relates to a method for reducing the number of daytime or nighttime chronic coughs in idiopathic/treatment-resistant chronic cough.

In one embodiment, the present invention relates to a method for reducing the number of daytime or nighttime chronic coughs in refractory cough, unexplained cough or idiopathic cough.

In one embodiment, the present invention includes a method of treating the neuronal hypersensitivity causing chronic cough.

In one embodiment, the present invention includes a method of treating the neuronal hypersensitivity causing refractory cough, unexplained cough or idiopathic cough.

In one embodiment, the present invention includes the compound represented by Formula (I) or a pharmaceutically acceptable salt thereof for use in reducing the number of daytime or nighttime chronic coughs in idiopathic/treatment-resistant chronic cough causing chronic cough, and for treating the neuronal hypersensitivity causing chronic cough.

In one embodiment, the present invention includes the compound represented by Formula (I) or a pharmaceutically acceptable salt thereof for use in reducing the number of daytime or nighttime chronic coughs in refractory cough, unexplained cough or idiopathic cough, and for treating the neuronal hypersensitivity causing refractory cough, unexplained cough or idiopathic cough.

In one embodiment, the present invention includes use of the compound represented by Formula (I) or a pharmaceutically acceptable salt thereof for the manufacture of a medicament for reducing the number of daytime or nighttime chronic coughs in idiopathic/treatment-resistant chronic cough, and for treating the neuronal hypersensitivity causing chronic cough.

In one embodiment, the present invention includes use of the compound represented by Formula (I) or a pharmaceutically acceptable salt thereof for the manufacture of a medicament for reducing the number of daytime or nighttime coughs in refractory cough, unexplained cough or idiopathic cough, and for treating the neuronal hypersensitivity causing refractory cough, unexplained cough or idiopathic cough.

As described in the Examples below, the present invention is characterized by a class of P2X$_3$ and/or P2X$_{2/3}$ receptor antagonists for treating or alleviating cough, including chronic cough, and the urge to cough. The present invention has the advantage of addressing the root causes of cough hypersensitivity in these diseases, rather than simply suppressing the central modulation involved in symptom perception. For example, the present invention provides a method of reducing afferent nerve activity that induces an urge to persistent and inadequate cough in sensitized subjects (for example, humans).

The present invention also has the advantage of producing substantially no taste-related side effects in sensitized subjects (for example, humans).

Furthermore, the compound represented by Formula (I) or a pharmaceutically acceptable salt thereof can be used for the treatment of not only chronic cough, but also acute and sub-acute cough.

EXAMPLES

Hereinafter, the present invention will be described based on examples. However, the present invention is not limited to these examples and the like.

Test Example 1 Phase I Clinical Trial

Thus far, two phase I studies have been completed. All studies were conducted based on Good Clinical Practice (GCP).

A summary of the clinical trials is shown in Table 1 below.

TABLE 1

| Clinical trial name | Clinical trial design | Country (Number of facilities) | Target | Dosage and administration | Number of subjects (Number of cases administered with the compound represented by Formula (I)) | Administration period | Purpose of clinical trial (Status) |
| --- | --- | --- | --- | --- | --- | --- | --- |
| Phase I Single Dose and Food Effect Study | Part A (Single Dose): Single-center, Randomized, Placebo-controlled, Double-blind Part B [Study of Relative Bioavailability (BA) and Effect of Food]: Single-center, Randomized, Open Label, Cross-over | Japan (1) | Japanese healthy adult males | Part A: 3, 10, 30, 100, 300, 450 mg or placebo; single oral administration of suspension under fasted condition Part B: 150 mg; single oral administration of suspension or tablets (50 mg tablets) under fasted or fed condition | Part A: 48 (36) Part B: 15 (15) | Part A: one day Part B: one time in one day × 3 days | Safety Tolerability Pharmacokinetics (Completed) |

TABLE 1-continued

| Clinical trial name | Clinical trial design | Country (Number of facilities) | Target | Dosage and administration | Number of subjects (Number of cases administered with the compound represented by Formula (I)) | Administration period | Purpose of clinical trial (Status) |
|---|---|---|---|---|---|---|---|
| Phase I Repeat Dose Study | Single-center, Randomized, Placebo-controlled, Double-blind | Japan (1) | Japanese and Caucasian healthy adult males | Japanese: 150, 300 mg; tablets (50 mg tablets) or placebo Caucasian: 150 mg; tablets (50 mg tablets) or placebo Single oral administration under fed condition, after 4 days, repeated oral administration for 14 days under fed condition | 30 (24) | 1 day and 14 days | Safety Tolerability Pharmacokinetics (Completed) |

(Results)

There were no deaths, serious adverse events, or adverse events leading to discontinuation of administration in either Part A or Part B of the Phase I single dose and food effect study.

There were no deaths, serious adverse events or adverse events leading to discontinuation of administration in any of the administration groups of the Phase I repeat dose study.

No taste-related adverse events or side effects were observed in all of these studies which have been conducted.

Test Example 2 Evaluation of Human $P2X_3$ Receptor Inhibitory Activity

A stably expressing cell line in which C6BU-1 cells have been transfected with human $P2X_3$ receptor gene (GenBank accession number Y07683) was seeded on a PDL-coated 96-well microplate so as to have 8000 cells per well, then cultured in medium (7.0% fetal bovine serum, 7.0% horse serum, 1% antibiotic-antimycotic mixed stock solution, DMEM containing 4.0 mM glutamine) at 37° C. and in 5% carbon dioxide for 1 day. The medium was replaced with a solution containing 4 µM of Fluo-3-AM (20 mM HEPES, 137 mM NaCl, 5.37 mM KCl, 0.9 mM $MgCl_2$, 1.26 mM $CaCl_2$, 5.6 mM D-glucose, 2.5 mM probenecid, 0.5% BSA, 0.04% Pluronic F-127, pH 7.5), then incubation was carried out at 37° C. and in 5% carbon dioxide for 1 hour. The wells were washed with wash buffer (20 mM HEPES, 137 mM NaCl, 5.27 mM KCl, 0.9 mM $MgCl_2$, 1.26 mM $CaCl_2$, 5.6 mM D-glucose, 2.5 mM probenecid, pH 7.5) and the microplate was filled with 40 µL of wash buffer per well. The microplate was placed in the high-throughput screening system FDSS 7000EX (Hamamatsu Photonics). The measurement of fluorescence intensity by FDSS 7000EX was started, and 40 µL per well of a DMSO solution of the compound represented by Formula (I) diluted with a dilution buffer (20 mM HEPES, 137 mM NaCl, 5.27 mM KCl, 0.9 mM $MgCl_2$, 1.26 mM $CaCl_2$, 5.6 mM D-glucose, 2.5 mM probenecid, 0.1% Pluronic F-127, pH 7.5) to different concentrations was each dispensed by the automatic pipetting device built in the FDSS 7000EX. After 5 minutes, 50 µL of ATP solution diluted with the dilution buffer (final concentration of 50 nM) was dispensed by the automatic pipetting device built in the FDSS 7000EX, and then the measurement of the fluorescence intensity was continued for 4 minutes. From the measured fluorescence intensity values, the specific maximum fluorescence intensity, which is expressed as the ratio of the maximum fluorescence intensity value after addition of the ATP solution to the fluorescence intensity at the start of measurement, was calculated for each microplate well. With the value of the specific maximum fluorescence intensity when the compound represented by Formula (I) is not contained as 0% inhibition, and the value of the specific maximum fluorescence intensity when the dilution buffer was added instead of ATP as 100% inhibition, the concentration for 50% inhibition ($IC_{50}$) was calculated to evaluate the inhibitory activity of the compound represented by Formula (I). The specific maximum fluorescence intensity was calculated using the FDSS software (Hamamatsu Photonics). The $IC_{50}$ was calculated using the software Microsoft Excel (Microsoft) and XLfit (idbs).

(Results)

The $IC_{50}$ was 0.004 µM.

Test Example 3 Evaluation of Human $P2X_{2/3}$ Receptor Inhibitory Activity

C6BU-1 cells were seeded on a PDL-coated 96-well microplate so as to have 3000 cells per well, then cultured in medium (7.0% fetal bovine serum, 7.0% horse serum, 1% antibiotic-antimycotic mixed stock solution, DMEM containing 4.0 mM glutamine) at 37° C. and in 5% carbon dioxide for 1 day. C6BU-1 cells were transfected with human $P2X_2$ receptor gene (GenBank accession number AF109387) and human $P2X_3$ receptor gene (GenBank accession number Y07683) using the transfection reagent FuGENE6 (manufactured by Promega), and further cultured at 37° C. in 5% carbon dioxide for 1 day. The medium was replaced with a solution containing 4 µM of Fluo-3-AM (20 mM HEPES, 137 mM NaCl, 5.27 mM KCl, 0.9 mM $MgCl_2$, 1.26 mM $CaCl_2$, 5.6 mM D-glucose, 2.5 mM probenecid, 1% BSA, 0.08% Pluronic F-127, pH 7.5), then incubation was carried out at 37° C. and in 5% carbon dioxide for 1 hour. The wells were washed with wash buffer (20 mM HEPES, 137 mM NaCl, 5.27 mM KCl, 0.9 mM $MgCl_2$, 1.26 mM $CaCl_2$, 5.6 mM D-glucose, 2.5 mM probenecid, pH 7.5) and the microplate was filled with 40 µL of wash buffer per well. The microplate is placed in the high-throughput screening system FDSS 7000EX (Hamamatsu Photonics). The measurement of fluorescence intensity by FDSS 7000EX was started, and 40 µL per well of a DMSO solution of the compound represented by Formula (I) diluted with a dilution buffer (20 mM HEPES, 137 mM NaCl, 5.27 mM KCl, 0.9 mM $MgCl_2$, 1.26 mM $CaCl_2$, 5.6 mM D-glucose, 2.5 mM probenecid, 0.1% Pluronic F-127, pH 7.5) to different concentrations was each dispensed by the automatic pipetting device built in the FDSS 7000EX. After 5 minutes, 50 µL of α,β-methylene ATP solution diluted with the dilution buffer (final concentration of 6 µM) was dispensed by the automatic pipetting device built in the FDSS 7000EX, and then the measurement of the fluorescence intensity was continued for 4 minutes. From the measured fluorescence intensity values, the specific maximum fluorescence intensity, which is expressed as the ratio of the maximum fluorescence intensity value after addition of the α,β-methylene ATP solution to the fluorescence intensity at the start of measurement, was calculated for each microplate well. With the value of the specific maximum fluorescence intensity when the compound represented by Formula (I) is not contained as 0% inhibition, and the value of the specific maximum fluorescence intensity when the dilution buffer was added instead of α,β-methylene ATP as 100% inhibition, the concentration for 50% inhibition ($IC_{50}$) was calculated to evaluate the inhibitory activity of the compound represented by Formula (I). The specific maximum fluorescence intensity was calculated using the FDSS software (Hamamatsu Photonics). The $IC_{50}$ was calculated using the software Microsoft Excel (Microsoft) and XLfit (idbs).
(Results)
The $IC_{50}$ was 1100 nM.

Test Example 4 Evaluation of Human $P2X_3$ Receptor Inhibitory Activity in the Presence of Human Serum Albumin (HSA)

A stably expressing cell line in which C6BU-1 cells have been transfected with human $P2X_3$ receptor gene (GenBank accession number Y07683) was seeded on a PDL-coated 96-well microplate so as to have 8000 cells per well, then cultured in medium (7.0% fetal bovine serum, 7.0% horse serum, 1% antibiotic-antimycotic mixed stock solution, DMEM containing 4.0 mM glutamine) at 37° C. and in 5% carbon dioxide for 1 day. The medium was replaced with a solution containing 4 μM of Fluo-3-AM (20 mM HEPES, 137 mM NaCl, 5.37 mM KCl, 0.9 mM $MgCl_2$, 1.26 mM $CaCl_2$, 5.6 mM D-glucose, 2.5 mM probenecid, 0.5% BSA, 0.04% Pluronic F-127, pH 7.5), then incubation was carried out at 37° C. and in 5% carbon dioxide for 1 hour. The wells were washed with wash buffer (20 mM HEPES, 137 mM NaCl, 5.27 mM KCl, 0.9 mM $MgCl_2$, 1.26 mM $CaCl_2$, 5.6 mM D-glucose, 2.5 mM probenecid, pH 7.5) and the microplate was filled with 40 μL of wash buffer per well. The microplate was placed in the high-throughput screening system FDSS 7000EX (Hamamatsu Photonics). The measurement of fluorescence intensity by FDSS 7000EX was started, and 40 μL per well of a DMSO solution of the compound of the present invention diluted to different concentrations with a solution of a dilution buffer (20 mM HEPES, 137 mM NaCl, 5.27 mM KCl, 0.9 mM $MgCl_2$, 1.26 mM $CaCl_2$, 5.6 mM D-glucose, 2.5 mM probenecid, 0.1% Pluronic F-127, pH 7.5) to which human serum albumin was added to a final concentration of 1%, was each dispensed by the automatic pipetting device built in the FDSS 7000EX. After 5 minutes, 50 μL of ATP solution diluted with the dilution buffer (final concentration of 50 nM) was dispensed by the automatic pipetting device built in the FDSS 7000EX, and then the measurement of the fluorescence intensity was continued for 4 minutes. From the measured fluorescence intensity values, the specific maximum fluorescence intensity, which is expressed as the ratio of the maximum fluorescence intensity value after addition of the ATP solution to the fluorescence intensity at the start of measurement, was calculated for each microplate well. With the value of the specific maximum fluorescence intensity when the compound represented by Formula (I) is not contained as 0% inhibition, and the value of the specific maximum fluorescence intensity when the dilution buffer was added instead of ATP as 100% inhibition, the concentration for 80% inhibition ($IC_{80}$) was calculated to evaluate the inhibitory activity of the compound represented by Formula (I). The specific maximum fluorescence intensity was calculated using the FDSS software (Hamamatsu Photonics). The $IC_{80}$ was calculated using the software Microsoft Excel (Microsoft) and XLfit (idbs).
(Results)
The $IC_{80}$ was 92.4 nM (46.9 ng/mL).

Test Example 5 Predicted Effective Dose for Humans

In the Phase I single dose study, 3, 10, 30, 100, 300, and 450 mg of the compound represented by Formula (I) was administered as a single dose, and the plasma concentration of the compound represented by Formula (I) in each subject 0.25, 0.5, 1, 1.5, 2, 2.5, 3, 3.5, 4, 5, 6, 8, 10, 12, 24, 36, 48, 72, and 120 hours after administration was measured over time. As a result, the maximum concentration was observed after 0.5 to 6 hours. When the compound represented by Formula (I) is administered once daily, the minimum plasma drug concentration at steady state is assumed to be the same as or higher than the plasma concentration 24 hours after the single dose. Therefore, the plasma concentration (geometric mean) after 24 hours is shown below. The plasma concentration after 24 hours at each dose was compared to 46.9 ng/mL, the $IC_{80}$ calculated in Test Example 4, which is considered as the concentration that sufficiently inhibits the $P2X_3$ receptor. As a result, 3 mg of the plasma concentration after 24 hours was lower than $IC_{80}$, but 10, 30, 100, 300, and 450 mg of the plasma concentration after 24 hours exceeded $IC_{80}$. Therefore, the minimum effective dose was set to 10 mg.
(Results)

TABLE 2

| Dosage of the compound represented by Formula (I), (mg) | The plasma concentration 24 hours after administration of the compound represented by Formula (I), (ng/mL), (geometric mean) |
|---|---|
| 3 | 15.2 |
| 10 | 50.7 |
| 30 | 134 |
| 100 | 424 |
| 300 | 1840 |
| 450 | 2680 |

In addition, in the Phase I single dose study, no dysgeusia or any taste-related disorder was observed as an adverse event in any of the dose groups of 3, 10, 30, 100, 300, and 450 mg. Moreover, in the Phase I repeat dose study, 150 and 300 mg of the compound represented by Formula (I) was repeatedly administered once daily for 2 weeks, and no dysgeusia or any taste-related disorder was observed. Therefore, the maximum effective dose with substantially no dysgeusia was set to 450 mg.

Test Example 6 Phase II Clinical Trial

A Phase II double-blind cross-over comparative study was conducted in patients with refractory/unexplained chronic cough.
In patients with refractory/unexplained chronic cough, the placebo-adjusted change from baseline in the number of coughs per hour during daytime (7 am to 7:59 pm, which means right before 8:00 pm) after 2 weeks of administration of the compound represented by Formula (I), and its significance were evaluated. Similarly, the placebo-adjusted change from baseline in the number of coughs per hour in 24 hours after administration of the compound represented by Formula (I) and its significance were also evaluated.

The placebo-adjusted change is defined by the following equation.

$$\text{Rate of change adjusted by placebo} = 100 \times \left[ \frac{100 + \text{Rate of change during administration of the compound representedd by Formula } (I) (\%)}{100 + \text{Rate of change during administration of placebo } (\%)} - 1 \right] (\%) \quad \text{[Expression 1]}$$

(Clinical Trial Design)

The trial was conducted as a placebo-controlled, multi-center, randomized, double-blind, cross-over comparative study. The study consists of a screening phase (1 to 4 weeks), a first treatment phase (15 days), a drug holiday (2 to 3 weeks), a second treatment phase (15 days) and a follow-up phase (1 week).

Subjects (20 females, 11 males, mean age of 50.0 years) were randomly assigned to either the group receiving the compound according to Formula (I) first or the group receiving the placebo first. The subjects in the group receiving the compound according to Formula (I) first received orally tablets containing 150 mg of the compound according to Formula (I) (50 mg, 3 tablets), and the subjects in the group receiving the placebo first received orally placebo tablets (3 tablets), from the day following the first treatment phase once daily in the morning for 2 weeks. Then, after 2 to 3 weeks of a drug holiday, during the second treatment phase, the subjects received orally the tablets which they did not receive in the first treatment phase, once daily in the morning for 2 weeks from the day following the second treatment phase.

(Results) A comparison (full analysis population) of the change in the number of coughs per hour during daytime is shown in Table 3 and FIG. 1.

TABLE 3

| Study drug | N = 31 | |
|---|---|---|
| | The compound represented by Formula (I) | Placebo |
| n | 31 | 30 |
| Estimated rate of change (%) | −54.1 | −33.0 |
| [95% CI] | [−66.7, −36.8] | [−51.6, −7.2] |
| Rate of change adjusted by placebo (%) | −31.6 | — |
| [95% CI] | [−53.6, 0.8] | — |
| P-value | 0.0546 | — |

(For the number of coughs per hour during daytime in each of the first and second treatment phases, the mixed effect model was applied, with the common logarithms of the ratio to the baseline after 2 weeks of administration as the responses, the investigational drugs, the administration groups (group receiving the compound represented by Formula (I) first and group receiving the placebo first), and phases as the fixed effects, the individuals as the random effects, and the common logarithms of the number of coughs per hour at baseline as the covariates.)

(Results) A comparison (full analysis population) of the change in the number of coughs per hour in 24 hours is shown in Table 4.

TABLE 4

| Study drug | N = 31 | |
|---|---|---|
| | The compound represented by Formula (I) | Placebo |
| n | 31 | 30 |
| Estimated rate of change (%) | −52.6 | −31.4 |
| [95% CI] | [−64.7, −36.3] | [−49.1, −7.4] |
| Rate of change adjusted by placebo (%) | −30.9 | — |
| [95% CI] | [−51.3, −2.1] | — |
| P-value | 0.0386 | — |

(For the number of coughs per hour in 24 hours in each of the first and second treatment phases, the mixed effect model was applied, with the common logarithms of the ratio to the baseline after 2 weeks of administration as the responses, the investigational drugs, administration groups (group receiving the compound represented by Formula (I) first and group receiving the placebo first), and phases as the fixed effects, the individuals as the random effects, and the common logarithms of the number of coughs per hour at baseline as the covariates.)

(Results) A comparison (full analysis population) of the total change in the sum of the three domains of the Leicester Cough Questionnaire [Japanese version] is shown in Table 5.

TABLE 5

| Study drug | N = 31 | |
|---|---|---|
| | The compound represented by Formula (I) | Placebo |
| n | 31 | 31 |
| Estimated amount of change | 2.46 | 1.06 |
| [95% CI] | [1.51, 3.41] | [0.11, 2.01] |
| Drug differences | 1.40 | — |
| [95% CI] | [0.06, 2.75] | — |
| P-value | 0.0415 | — |

(For the change from baseline in the total score of the three domains of the Leicester Cough Questionnaire [Japanese version] at the end or discontinuation of each of the first and second treatment phases, the mixed effect model was applied, with the changes from the baseline as the responses, the investigational drugs, phases, and administration groups (group receiving the compound represented by Formula (I) first and group receiving the placebo first) as the fixed effects, the individuals as the random effects, and the total scores of the three domains of the Leicester Cough Questionnaire [Japanese version] at baseline as the covariates.)

As shown in Table 3 and FIG. 1, the placebo-adjusted rate of decrease in the number of coughs per hour during daytime was 31.6%.

As shown in Table 4, the placebo-adjusted rate of decrease in the number of coughs per hour in 24 hours was 30.9%, and a significant difference was observed.

As shown in Table 5, the difference between the investigational drug groups in the total score of the three domains of the Leicester Cough Questionnaire was 1.40 points, and a significant difference was observed.

Moreover, the efficacy of the compound according to Formula (I) and the placebo can be compared based on the following evaluation indexes for the patients with refractory/unexplained chronic cough described above.

Examples of evaluation indexes include the number of coughs per hour during nighttime, the number of coughs per hour during waking hours, the number of coughs per hour during sleeping hours, the severity assessment using the Cough Visual Analog Scale (VAS), the Patient Global Impression of Change (PGIC), and the European Quality of Life Questionnaire 5-Dimension 5-Level (EQ-5D-5L).

Next, the incidence of taste-related adverse events and side effects observed in the Phase II clinical trial is shown in Table 6.

TABLE 6

| System Organ Class [a] - Preferred Term | The compound represented by Formula (I) N = 31 | | Placebo N = 31 | |
|---|---|---|---|---|
| | n (%) | (n) | n (%) | (n) |
| Patients with any Treatment - related AEs | 4 (12.9) | (4) | 1 (3.2) | (1) |
| Nervous system disorders | 2 (6.5) | (2) | 0 | (0) |
| Dysgeusia | 1 (3.2) | (1) | 0 | (0) |
| Hypogeusia | 1 (3.2) | (1) | 0 | (0) |
| Gastrointestinal disorders | 1 (3.2) | (1) | 1 (3.2) | (1) |
| Hypoaesthesia oral | 1 (3.2) | (1) | 1 (3.2) | (1) |
| Hepatobiliary disorders | 1 (3.2) | (1) | 0 | (0) |
| Drug-induced liver injury | 1 (3.2) | (1) | 0 | (0) |

Note:
"Treatment-related AE" is defined as an event in which causality cannot be denied among adverse events reported after initial administration of study drugs.
(n): Number of events
[a] System organ class and Preferred term of MedDRA Ver. 21.0

As shown in Table 6, taste-related adverse events were observed in 2 subjects during at the administration of the compound represented by Formula (I), but both were mild. The taste-related adverse events were dysgeusia (taste change) and hypogeusia, which were observed in 3.2% and 3.2% of patients, respectively.

Here, the incidence of taste-related adverse events in Test Example 6 was examined. In this study, the compound represented by Formula (I) and the corresponding placebo were used as the investigational drugs. As the study design, a cross-over design consisting of two treatment phases was used. Each subject was assigned to either the treatment group taking 150 mg per day of the compound represented by Formula (I) during the first treatment phase and the placebo during the second treatment phase, or the treatment group taking the placebo during the first treatment phase and 150 mg per day of the compound represented by Formula (I) during the second treatment phase. The safety analysis population in this study was 31 subjects, all of whom were taking the compound represented by Formula (I) and the placebo. Among them, dysgeusia occurred in 1 subject (1/31, 3.2%) and hypogeusia occurred in another subject (1/31, 3.2%) when taking the compound represented by Formula (I). No ageusia was observed. Therefore, taste-related adverse events occurred in 2 subjects (2/31, 6.5%). No taste-related adverse events were observed when taking the placebo.

On the other hand, in the study MK-7264-012 (ClinicalTrials.gov, identification number NCT02612610), Gefapixant and the corresponding placebo were used as the investigational drugs. As the study design, a parallel-group design consisting of four treatment groups: Gefapixant 7.5 mg, 20 mg, 50 mg, and placebo was used. Each subject was assigned to take any of these twice daily. The number of subjects in the safety analysis, and the number of subjects and the incidence of taste-related adverse events in the Gefapixant 50 mg group and the placebo group are shown in Table 7. (Number of subjects and the incidence of taste-related adverse events in the Gefapixant 50 mg group and the placebo group (Reference: Non-patent Document 25))

TABLE 7

| | Gefapixant 50 mg group | Placebo group |
|---|---|---|
| Number of subjects in safety analysis | 63 | 63 |
| Ageusia | 13 (20.6%) | 1 (1.6%) |
| Dysgeusia | 30 (47.6%) | 3 (4.8%) |
| Hypogeusia | 15 (23.8%) | 1 (1.6%) |
| Any of taste-related adverse events | 51 (81.0%) | 4 (6.3%) |

Based on the above results, for the proportion of subjects who experienced any of the taste-related adverse events, the study design of each study was taken into account, and as the difference between each investigational drug and placebo, the mean of differences of incidence in the same subject between the treatments and the two-sided 95% confidence interval thereof were calculated for Test Example 6, and the difference of incidence between the Gefapixant 50 mg treatment group and the placebo treatment group and the two-sided 95% confidence interval thereof were calculated for the study MK-7264-012. The results are shown in Table 8. As can be seen in Table 8, the 95% confidence upper limit of the difference with the placebo in the incidence of any of the taste-related adverse events obtained from Test Example 6, 15.6%, was well below the 95% confidence lower limit of 63.2% obtained from the study MK-7264-012.

(Difference Between Each Investigational Drug and Placebo in the Incidence of any the Taste-Related Adverse Events)

TABLE 8

| Study name: Method of calculating difference | Difference of incidence | 95% confidence lower limit | 95% confidence upper limit |
|---|---|---|---|
| Test Example 6: Difference between treatments * (150 mg of compound represented by Formula (I) − placebo) | 6.5% | −2.7% | 15.6% |
| Study MK-7264-012: Difference between treatment groups (Gefapixant 50 mg − placebo) | 74.6% | 63.2% | 86.0% |

* Defined as the mean of the difference between the value when taking the compound represented by Formula (I) and the value when taking the placebo in each subject, and the 95% confidence interval, with 1 indicating the occurrence of any of the taste-related adverse events and 0 indicating that no adverse events occurred.

From the above results, it can be expected that the incidence of any of the taste-related adverse events is extremely low with 150 mg of the compound represented by Formula (I) compared to 50 mg of Gefapixant.

In addition, the taste-related adverse events observed in Test Example 6 accounted for 6.5% (2/31) of patients, which was similar to the 6.3% (4/63) for the adverse events observed during placebo administration in the study MK-7264-012.

FORMULATION EXAMPLE

The following Formulation Examples are only exemplified and not intended to limit the scope of the invention.

(Formulation Example 1) Suspension

For example, water for injection was added to the active pharmaceutical ingredient, the compound represented by Formula (I), to prepare a suspension.

(Formulation Example 2) Tablets

For example, lactose and magnesium stearate were added as additives to the active pharmaceutical ingredient, the compound represented by Formula (I), to prepare tablets.

INDUSTRIAL APPLICABILITY

The method for treating chronic cough of the present invention and the pharmaceutical composition for the treatment used therefor is considered to exhibit an excellent therapeutic effect by administering a predetermined amount of the active ingredient, the compound represented by Formula (I) or a pharmaceutically acceptable salt thereof, to patients with chronic cough. In addition, having substantially no taste-related side effects from the administration of the compound represented by Formula (I) or a pharmaceutically acceptable salt thereof, the treatment method and pharmaceutical composition for the treatment of the present invention can be applied extremely safely, and are also suitable for long-term administration. Therefore, they are an excellent treatment method and pharmaceutical composition for the treatment.

The invention claimed is:

1. A method for treating chronic cough, the method comprising a step of administering an effective amount of a compound represented by Formula (I):

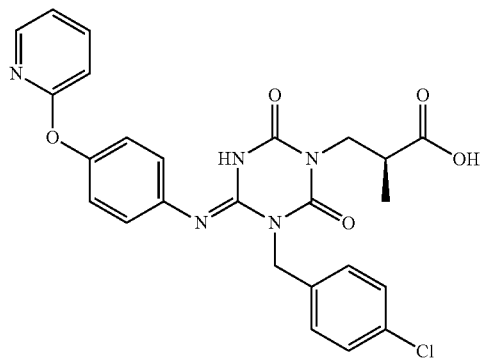

or a pharmaceutically acceptable salt thereof as an active ingredient to an individual in need of treatment of chronic cough,
wherein the effective amount of the active ingredient is a daily dose of 10 mg to 450 mg.

2. The method of treatment according to claim 1, wherein the chronic cough is a refractory chronic cough.

3. The method of treatment according to claim 1, wherein the compound represented by Formula (I) or the pharmaceutically acceptable salt thereof has substantially no side effects of taste disturbance by the administration of the compound or salt thereof.

4. The method of treatment according to claim 1, which is administered once daily.

5. The method of treatment according to claim 1, wherein the effective amount of the active ingredient is a daily dose of 50 mg to 300 mg.

6. The method of treatment according to claim 1, wherein the effective amount of the active ingredient is a daily dose of 50 mg to 150 mg.

7. The method of treatment according to claim 1, wherein the effective amount of the active ingredient is a daily dose of 150 mg to 300 mg.

8. The method of treatment according to claim 1, which is administered once daily after a meal.

9. The method of treatment according to claim 1, which is administered once daily at bedtime.

10. The method of treatment according to claim 1, wherein the cough is a 24-hour cough.

11. The method of treatment according to claim 1, wherein the cough is a daytime cough.

* * * * *